US006473176B2

(12) United States Patent
Basiji et al.

(10) Patent No.: US 6,473,176 B2
(45) Date of Patent: *Oct. 29, 2002

(54) IMAGING AND ANALYZING PARAMETERS OF SMALL MOVING OBJECTS SUCH AS CELLS

(75) Inventors: David A. Basiji, Seattle, WA (US); William E. Ortyn, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/820,434

(22) Filed: Mar. 29, 2001

(65) Prior Publication Data

US 2001/0021018 A1 Sep. 13, 2001

Related U.S. Application Data

(63) Continuation-in-part of application No. 09/538,604, filed on Mar. 29, 2000, now Pat. No. 6,211,955, which is a continuation-in-part of application No. 09/490,478, filed on Jan. 24, 2000, now Pat. No. 6,249,341.
(60) Provisional application No. 60/117,203, filed on Jan. 25, 1999.

(51) Int. Cl.[7] .............................. G01J 3/12; G01J 3/28
(52) U.S. Cl. ...................................... 356/326; 356/419
(58) Field of Search ................. 356/416, 417, 356/419; 359/633, 634; 348/336, 338, 340; 358/515; 250/226

(56) References Cited

U.S. PATENT DOCUMENTS

| 4,284,323 A | * | 8/1981 | Jankowitz ................... 359/360 |
| 4,746,798 A | * | 5/1988 | Amon et al. ............ 250/339.02 |
| 4,786,165 A | | 11/1988 | Yamamoto et al. ............ 356/23 |
| 5,159,397 A | | 10/1992 | Kosaka et al. ................. 356/73 |
| 5,159,398 A | | 10/1992 | Maekawa et al. .............. 356/73 |
| 5,159,642 A | | 10/1992 | Kosaka ........................... 382/6 |
| 5,247,339 A | | 9/1993 | Ogino ........................... 356/73 |
| 5,272,354 A | | 12/1993 | Kosaka ........................ 250/574 |
| 5,422,712 A | | 6/1995 | Ogino ........................... 356/73 |
| 5,444,527 A | | 8/1995 | Kosaka .......................... 356/73 |
| 5,471,294 A | | 11/1995 | Ogino ........................... 356/73 |
| 5,548,395 A | | 8/1996 | Kosaka .......................... 356/73 |
| 5,596,401 A | | 1/1997 | Kusuzawa ................... 356/23 |

(List continued on next page.)

FOREIGN PATENT DOCUMENTS

WO    WO 00/42412    7/2000    ........ G01N/15/02

OTHER PUBLICATIONS

Ong, S.–H.; Horne, D.; Yeung, C.–K.; Nickolls; P., Cole, T. "Development of an Imaging Flow Cytometer." Analytical and Quantitative Cytology and Histology. XIVth International Conference on Medical and Biological Engineering and the VIIth International Conference on Medical Physics, Espoo, Finland. Aug. 11–15, 1985, pp. 375–382.

Ong, Sim Heng. "Development of a System for Imaging and Classifying Biological Cells in a Flow Cytometer." Doctor of Philosophy Thesis. University of Sydney, School of Electrical Engineering. Aug. 1985.

*Primary Examiner*—F. L. Evans
(74) *Attorney, Agent, or Firm*—Ronald M. Anderson

(57) ABSTRACT

Light from an object such as a cell moving through an imaging system is collected and dispersed so that it can be imaged onto a detector. The light can be emitted from a luminous object or can be light from a light source that has been scattered or not absorbed by the object or can include a light emission by one or more probes within or on the object. Multiple objects passing through the imaging system can be imaged, producing both scatter images and dispersed images at different locations on one or more detectors. In one embodiment, the detector is divided into a plurality of zones so that each of a plurality of different images are spectrally dispersed onto a different zone of the detector.

40 Claims, 19 Drawing Sheets

U.S. PATENT DOCUMENTS

| | | | |
|---|---|---|---|
| 5,633,503 A | 5/1997 | Kosaka | 250/458.1 |
| 5,644,388 A | 7/1997 | Maekawa et al. | 356/73 |
| 5,754,291 A | 5/1998 | Kain | 356/338 |
| 5,760,899 A | 6/1998 | Eismann | 356/326 |
| RE35,868 E | 8/1998 | Kosaka | 250/574 |
| 5,831,723 A | 11/1998 | Kubota et al. | 356/73 |
| 5,926,283 A * | 7/1999 | Hopkins | 356/419 |
| 6,116,739 A * | 9/2000 | Ishihara et al. | 353/31 |
| 6,211,955 B1 * | 4/2001 | Basiji et al. | 356/326 |

* cited by examiner

IMAGING AND ANALYZING PARAMETERS OF SMALL MOVING OBJECTS SUCH AS CELLS

RELATED APPLICATIONS

This application is a continuation-in-part application of a copending patent application Serial No. 09/538,604, filed Mar. 29, 2000 now U.S. Pat. No. 6,211,955, which is a continuation-in-part application of prior copending patent application Serial No. 09/490,478, filed on Jan. 24, 2000 now U.S. Pat. No. 6,249,341, which is based on provisional application Serial No. 60/117,203, filed on Jan. 25, 1999, the benefit of the filing dates of which is hereby claimed under 35 U.S.C. § 120 and 35 U.S.C. § 119(e).

FIELD OF THE INVENTION

This invention generally relates to imaging moving objects or particles for purposes of analysis and detection, and more specifically, to a system and method for determining and analyzing the morphology of moving objects, such as cells, and for detecting the presence and composition of Fluorescence In-Situ Hybridization (FISH) probes within cells.

BACKGROUND OF THE INVENTION

There are a number of biological and medical applications that are currently impractical due to limitations in cell and particle analysis technology. Examples of such biological applications include battlefield monitoring of known airborne toxins, as well as the monitoring of cultured cells to detect the presence of both known and unknown toxins. Medical applications include non-invasive prenatal genetic testing and routine cancer screening via the detection and analysis of rare cells (i.e., low rate of occurrence) in peripheral blood. All of these applications require an analysis system with the following principal characteristics:

1. high speed measurement;
2. the ability to process very large or continuous samples;
3. high spectral resolution and bandwidth;
4. good spatial resolution;
5. high sensitivity; and
6. low measurement variation.

In prenatal testing, the target cells are fetal cells that cross the placental barrier into the mother's bloodstream. In cancer screening, the target cells are sloughed into the bloodstream from nascent cancerous tumors. In both of these applications of this technology, the target cells may be present in the blood at concentrations of one to five cells per billion. This concentration yields approximately 20–100 target cells in a typical 20 ml blood sample. The extreme rarity of the targeted cells demands that any detection and analysis system employed in these applications be capable of processing an enriched sample of approximately 100 million cells within a few hours, corresponding to a minimum throughput of 10,000 cells per second. Cell processing includes the determination of cellular morphology parameters such as overall size, nuclear size, nuclear shape, and optical density, the detection and characterization of numerous fluorescent markers and FISH probes, the quantification of the total amount of DNA in the nucleus, and the detection of other cellular components such as fetal hemoglobin. To accomplish these processing tasks, the system must be able to collect cell images with a spatial resolution of approximately 1 micron. Likewise, the system must have high spectral resolution and bandwidth to differentiate four or more fluorescent colors. Since some probes may label important cellular features with only a few thousand fluorescent molecules, the system must have high sensitivity and good measurement consistency to differentiate very weak signals.

The predominant research laboratory protocols for non-invasive prenatal diagnosis employ a complex series of process steps that include gradient centrifugation to remove unnucleated cells, high speed cell sorting for fetal cell enrichment, and fluorescence microscopy for fetal cell identification and genetic analysis. These protocols often yield little or no fetal cells for analysis, because a fraction of the fetal cells are lost at each step of the protocol. Nevertheless, the protocols cannot be simplified because of limitations in existing analysis technology. Ideally, fetal cell identification and analysis would be performed in a few hours by a high speed cell sorter having the necessary speed and sample handling capacity. This ideal is not possible with conventional systems, because conventional cell sorters lack the necessary imaging abilities, sensitivity, and repeatability to reliably identify fetal cells and enumerate the number and color of FISH probes used to make the diagnosis. Therefore, under current protocols, cells must be sorted onto slides and examined using fluorescence microscopy to establish their fetal origin and make a genetic diagnosis. The combination of low fetal cell yields and lengthy processing times precludes the clinical application of non-invasive fetal testing with existing technology.

No technology prior to the present invention incorporates all six of the principal characteristics of a viable fetal cell or cancer analysis system. In the prior art, there have been advances that might be applied to these applications, but significant limitations still remain.

A paper published by Ong et al. [Anal. Quant. Cytol. Histol., 9(5):375–82] describes the use of a time delay and integration (TDI) detector in an imaging flow cytometer. A TDI detector is any pixilated device in which the signal produced in response to radiation directed at the device can be caused to move in a controlled fashion. Typically, the pixels of a TDI detector are arranged in rows and columns, and the signal is moved from row to row in synchrony with a moving image projected onto the device, allowing an extended integration time without blurring. The approach disclosed by Ong et al. advanced the art by addressing the need for spatial resolution and high sensitivity for cells in flow. However, this approach does not address the remaining principal characteristics. The authors of this paper cite an operating speed of 10 cells per second and a theoretical speed limitation of 500 cells per second, which is at least an order of magnitude slower than is required for non-invasive fetal testing. In addition, the system has no spectral resolution; laser scatter and fluorescent light are collected by the imaging system indiscriminately.

In more recent developments, U.S. Pat. No. 5,644,388 discloses an alternative approach to an imaging flow cytometer. The patent discloses the use of a frame-based image collection approach in which a video camera views cells in flow, in a freeze frame fashion. This method requires the image collection system to be synchronized with the presence of cells in the imaging area, unlike the case of TDI, wherein the detector readout rate is synchronized with the velocity of the cells. When a cell is imaged with the frame-based method, the integration period must be very short to prevent blurring. A short integration time is achieved either with a strobed light source, or a continuous light source combined with a shuttered detector. In either case, the short integration time reduces the signal-to-noise ratio and the ultimate sensitivity of the approach. Further, frame-based cameras require time to transfer data out of the camera, during which no images are acquired, and cells of interest can escape detection. Finally, like the work of Ong et al., this patent makes no provisions for acquiring data over a large spectral bandwidth and with sufficient spectral resolution to simultaneously resolve numerous and differently colored fluorescent probes and FISH spots.

Spectral discrimination is addressed in U.S. Pat. No. 5,422,712, in which the spectra of particles suspended in a fluid are collected as the particles flow through a detection region. However, there is no spatial representation of the object in the system disclosed in this patent, because the object is defocussed at the detector. In this system, light is collected from the object and an image is created at an intermediate aperture. The light continues through the aperture to a spectral dispersing element, which disperses the light spectrally along the axis of flow. The dispersed light is applied to an image intensifier in which it is amplified, and the light signal output from the image intensifier is finally directed to a frame-based detector. At the intermediate aperture, prior to spectral dispersion, the image represents the spatial distribution of light in object space. The spatial distribution is blurred as the light propagates past the image plane, through the spectral dispersing element and onto the image intensifier. Because there is no provision for re-imaging the intermediate aperture at the intensifier, the resulting signal distribution at the intensifier represents only the spectral distribution of the light and does not preserve the spatial distribution of the light from the object. The loss of spatial information limits the utility of the invention for applications such as fetal cell analysis. If multiple identical FISH spots are present in a cell, their spectra can be ascertained using this approach, but the number of spots cannot be determined. In addition, this approach disperses the wavelength spectrum parallel to the axis of flow. If two particles are illuminated in the flow axis, their spectra can overlap on the detector. To prevent this problem, the patent discloses that a very short illumination height in the flow axis is used. The short illumination height decreases integration time, which necessitates the use of the image intensifier. Further, the short illumination height limits throughput by preventing the simultaneous imaging of multiple cells in the flow axis.

Accordingly, it will be apparent that an improved technique is desired that resolves the limitations of the conventional approaches discussed above. It is expected that the new approach developed to address these problems in the prior art will also have application to the analysis of other types of moving objects besides cells and may be implemented in different configurations to meet the specific requirements of disparate applications of the technology.

SUMMARY OF THE INVENTION

The present invention is directed to an imaging system that is adapted to determine one or more characteristics of an object from an image of the object. There is relative movement between the object and the imaging system, and although it is contemplated that either (or both) may be in motion, the object will preferably move while the imaging system will be fixed. In addition, it should also be understood that while much of the following summary and the corresponding claims recite "an object," it is clearly contemplated that the present invention is preferably intended to be used with a plurality of objects and is particularly useful in connection with imaging a stream of objects.

The present invention provides a method and apparatus for the analysis of rare cells in the blood for the purposes of non-invasive fetal cell diagnosis and cancer screening, as well as other applications. To achieve such functions, the present invention is capable of rapidly collecting data from a large cell population with high sensitivity and low measurement variation. These data include simultaneous spatial and spectral images covering a large bandwidth at high resolution. Further, the present invention preserves the spatial origin of the spectral information gathered from the object.

Several different embodiments of the imaging system are provided. One preferred form of the invention includes a collection lens disposed so that light traveling from the object is collimated by passing through the collection lens and travels along a collection path. A spectral dispersing element is disposed in the collection path so as to spectrally disperse the collimated light that has passed through the collection lens in a plane substantially orthogonal to a direction of relative movement between the object and the imaging system, producing spectrally dispersed light. (As noted above, the object or the imaging system or both can be in motion relative to the other and for the sake of simplicity, this relative movement is hereinafter referred to simply as "the movement.") An imaging lens is disposed to receive the spectrally dispersed light, producing an image from the spectrally dispersed light. Also included is a TDI detector disposed to receive the image produced by the imaging lens. As the movement occurs, the image of the object produced by the imaging lens moves from row to row across the TDI detector. The TDI detector produces an output signal that is indicative of at least one characteristic of the object, by integrating light from at least a portion of the object over time.

As a result of light collimation by the collection lens in this embodiment, all light emitted from a first point in the object travels in parallel rays. Light emitted from a second point in the object will also travel in parallel rays, but at a different angle relative to light from the first point. In this manner, spatial information in the object is transformed by the collection lens into angular information in the collection path. The spectral dispersing element acts on the collimated light such that different spectral components leave the spectral dispersing element at different angles, in a plane substantially orthogonal to the direction of the movement between the object and the imaging system. In this manner, both spatial and spectral information in the object are transformed into angular information. The imaging lens acts on the light from the dispersing element to transform different light angles into different positions on the detector. Spatial information is preserved by the system since light from the different positions in the object is projected to different positions on the detector, for both axes. In addition, light of different spectral composition that originates from the object is projected to different positions on the detector in an axis substantially orthogonal to the movement. In this manner, the spatial information from the object is preserved, while spectral information covering a large bandwidth is simultaneously collected at high resolution.

FIG. 16 further illustrates the simultaneous collection of spectral and spatial information by the present invention, when imaging male and female cells 200 and 208, respectively. Light of shorter wavelength, such as green laser scatter 212, will be focussed on the left side of the TDI detector. Light of slightly longer wavelength, such as yellow fluorescence 214 from a cell nucleus 202 or 210, will be laterally offset to the right. Light of still longer wavelengths, such as orange fluorescence 216 from an X-chromosome FISH probe and red fluorescence 218 from a Y-chromosome FISH probe, will be focussed progressively farther to the right on the TDI detector. In this manner, different components of a cell that fluoresce at different wavelengths will be focussed at different locations on the TDI detector, while preserving the spatial information of those components. Each component image may be broadened laterally due to the width of its associated fluorescence emission spectrum. However, this broadening can be corrected based upon a priori knowledge of the emission spectra. Deconvolution of the emission spectrum from the broadened component image will yield an undistorted component image. Further, since the spectral dispersion characteristics of the spectral dispersing element are known, the lateral offsets of the different color component images can be corrected to reconstruct an accurate image of the cell. Using this embodiment of the invention, high spatial resolution information can be collected simultaneously with high spectral resolution over several hundred nanometers of spectral bandwidth. It should clear to those skilled in the art that the present invention can be employed to enumerate numerous and multicolored FISH probes to simultaneously determine many characteristics from cells.

In the following disclosure, for all forms of the present invention where a prism is used as a spectral dispersing element, it can be replaced with a spectral dispersing component having characteristics that ensure no distortion or convolution of the image occurs due to the emission bandwidth, and as a result, a deconvolution is not needed to correct the image. Preferably, the spectral dispersing component employed comprises a plurality of dichroic beam splitters, such as dichroic mirrors, which are arranged to reflect light within predefined bandwidths at predefined angles. Unlike a prism, where every wavelength leaves the prism at a different angle, all light within a predefined bandwidth incident on the dichroic beam splitter at a common angle leaves a given dichroic beam splitter at the same angle. Therefore, there is no convolution between the emission spectrum of the light leaving the object and the image of that object. When using such a spectral dispersing component, light of a first spectral bandwidth reflects off the first dichroic beam splitter at a predefined nominal angle. Light of a second spectral bandwidth is passed through the first dichroic beam splitter to the next dichroic beam splitter and is reflected therefrom at a different predefined nominal angle. Light of a third spectral bandwidth is passed through the first and second dichroic beam splitters to a third dichroic beam splitter and reflected therefrom at a third predefined nominal angle. The dichroic beam splitters are selected to cover the desired light spectrum with the appropriate spectral passbands. The angle of each dichroic beam splitter is set such that light reflected from it within the corresponding spectral bandwidth for the dichroic beam splitter is focussed onto a different region of the detector. Since the present invention uses a narrow field angle in object space along the axis perpendicular to the axis of motion, many different spectral bandwidths can be simultaneously imaged onto a single detector. In this manner, each region on the detector may cover a different spectral bandwidth while collecting light over the same field angle in object space.

Depending on the amount of out-of-band rejection required, a bandpass filter is optionally placed in front of the detector. In one embodiment, the bandpass filter comprises a plurality of narrow spectral filters placed side-by-side to cover regions of the detector in correspondence with the spectral information to be imaged in those regions. Since the position of each spectral bandwidth region is predefined, and since the present invention maintains the spatial integrity of the object, a full color, high spectral resolution representation of the object is generated from the spectral information imaged onto the detector.

The use of a TDI detector in the present invention results in an extended imaging region along the axis of motion and a correspondingly long integration time. Several light sources can be simultaneously projected into the imaging region, increasing the amount of light incident upon objects therein. In addition, the combination of an extended imaging region and the orthogonal orientation of the spectral dispersion axis relative to the axis of the motion allows multiple objects to be imaged simultaneously. The long integration time and parallel image acquisition of this embodiment allows sensitive and consistent imaging performance to be combined with high throughput.

There are several alternative ways to provide light from the object. In one case, the light from the object comprises an unstimulated emission from the object, i.e., the object emits light without requiring a light source to stimulate the emission. In another embodiment, a light source is disposed to provide an incident light that illuminates the object. In this case, the object may scatter the incident light so that the light scattered from the object at least in part passes through the collection lens, or the incident light illuminating the object may stimulate the object to emit the light that passes through the collection lens. Further, the incident light may at least be partially absorbed by the object, so that the light passing through the collection lens does not include a portion of the light absorbed by the object. Finally, the incident light from the light source may be reflected from the object toward the collection lens. The light source or sources that are used preferably comprise at least one of a coherent light source, a non-coherent light source, a pulsed light source, and a continuous light source.

Spectral dispersion may be accomplished by many means, including a prism or grating. Further, although one preferred form of the invention employs a spectral dispersing element, the present invention is not limited to imaging the spectral dispersion of light. Alternatively, a dispersing element can be used to disperse light as a function of position, angle, polarization, phase, and other properties.

The object may be entrained within a fluid stream that moves the object past the collection lens, or alternatively, can be carried on a support, or simply move without the benefit of a support or flowing medium. Moreover, the present invention is not limited to the imaging of microscopic or small objects.

The TDI detector preferably responds to the image of the object by producing a signal that propagates across the TDI detector. Pixels of a typical TDI detector are arranged in rows and columns, and the signal propagates from row to row. However, the present invention is not limited to TDI detectors employing a rectilinear arrangement of pixels (e.g., a microchannel plate-based TDI detector). A propagation rate of the signal across the TDI detector can either be synchronized with a motion of the image of the object on the TDI detector as a result of the movement, or can be non-synchronized with the movement.

Other aspects of the present invention are directed to methods for imaging an object. These methods implement steps that are generally consistent with the imaging system discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

The present invention offers considerable advantages over systems employed for cell and particle analysis in the prior art. These advantages arise from the use in the present invention of an optical dispersion system in combination with a TDI detector that produces an output signal in response to the images of cells and other objects that are directed on the TDI detector. Multiple objects can be imaged on the TDI detector at the same time. In addition, the image of each object can be spectrally decomposed to discriminate object features by absorption, scatter, reflection or probe emissions using a common TDI detector for analysis.

The present invention can be employed to determine morphological, photometric, and spectral characteristics of cells and other objects by measuring optical signals including light scatter, reflection, absorption, fluorescence, phosphorescence, luminescence, etc. Morphological parameters include nuclear area, perimeter, texture or spatial frequency content, centroid position, shape (i.e., round, elliptical, barbell-shaped, etc.), volume, and ratios of any of these parameters. Similar parameters can also be determined for the cytoplasm of cells with the present invention. Photometric measurements with the invention enable the determination of nuclear optical density, cytoplasm optical density, background optical density, and the ratios of any of these values. An object being imaged with the present invention can either be stimulated into fluorescence or phosphorescence to emit light, or may be luminescent, producing light without stimulation. In each case, the light from the object is imaged on the TDI detector of the present invention to determine the presence and amplitude of the emitted light, the number of discrete positions in a cell or other object from which the light signal(s) originate(s), the relative placement of the signal sources, and the color (wavelength or waveband) of the light emitted at each position in the object.

An initial application of the imaging system comprising the present invention will likely be employed as a cell analyzer to determine one or more of the parameters listed above, for cells entrained in a fluid flowing through the imaging system. However, it should also be understood that this invention can be used for imaging other moving objects.

First Preferred Embodiment

Figure 1:
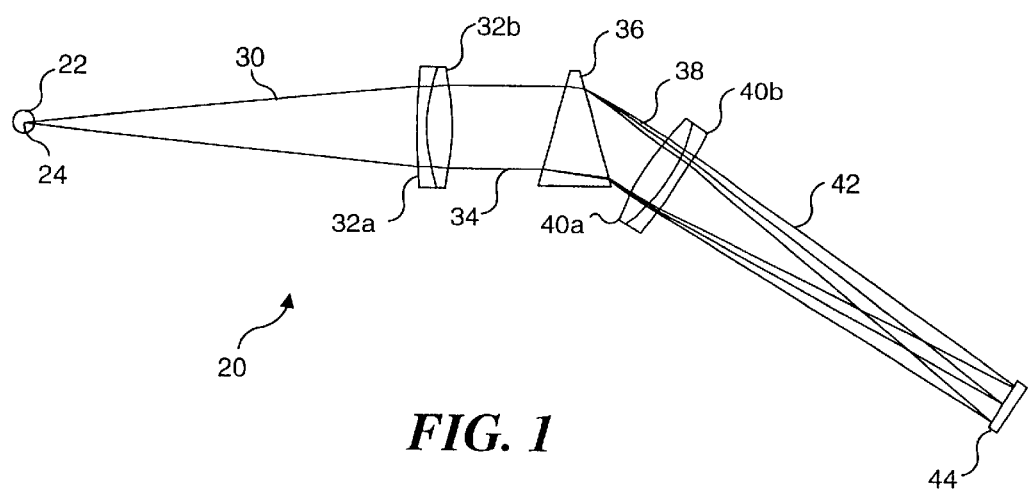
FIG. 1 is a plan view of a first embodiment of the present invention in which particles conveyed by a fluid stream depicted as flowing into the sheet.
Figure 2:
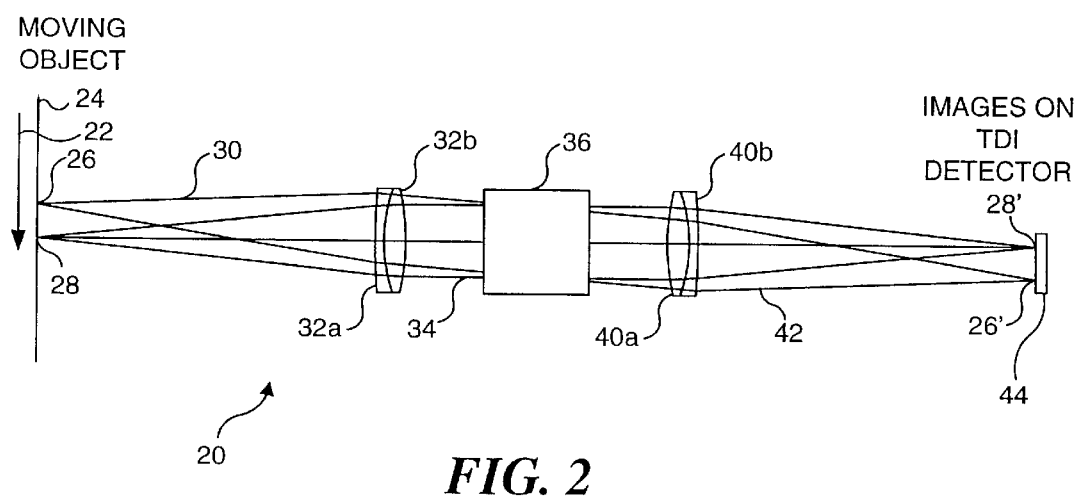
FIG. 2 is a side elevational view of the first embodiment shown in FIG. 1.
Figure 3:
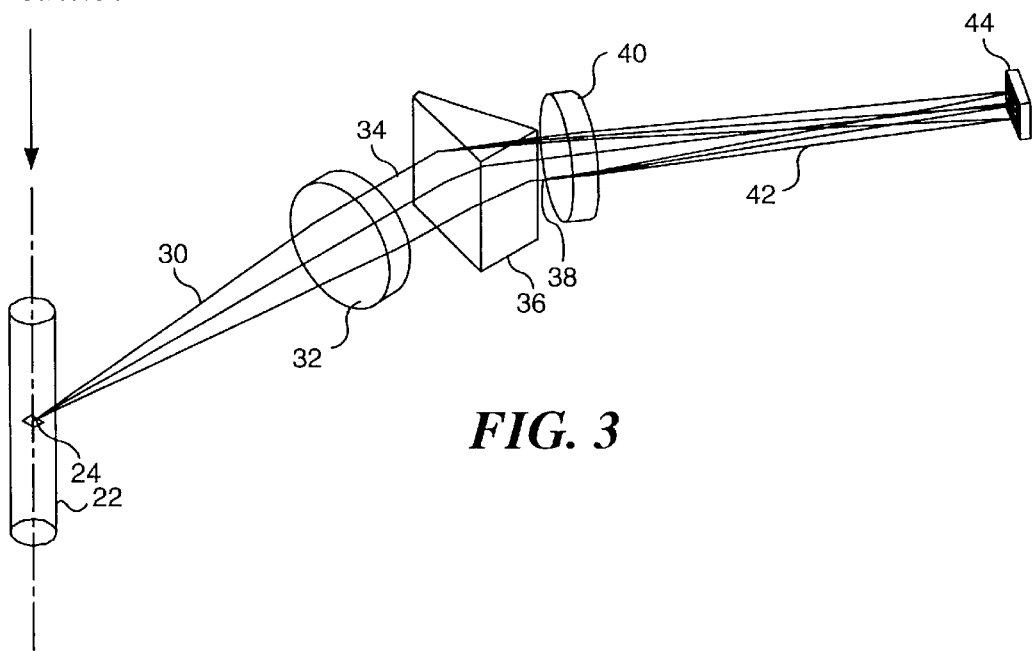
FIG. 3 is an isometric view of the first embodiment of FIG. 1.

A first preferred embodiment of an imaging system 20 in accord with the present invention is schematically illustrated in FIGS. 1, 2, and 3, in connection with producing images of moving objects such as cells that are conveyed by a fluid flow 22 through the imaging system. In FIG. 1, fluid flow 22 entrains an object 24 (such as a cell, but alternatively, a small particle) and carries the object through the imaging system. The direction of the fluid flow in FIG. 1 is into (or out of) the sheet, while in FIGS. 2 and 3, the direction of flow is from top to bottom, as indicated by the arrow to the left of the Figures. Light 30 from object 24 passes through collection lenses 32a and 32b that collect the light, producing collected light 34, which is approximately focussed at infinity, i.e. the rays of collected light from collection lens 32b are generally parallel. Collected light 34 enters a prism 36, which disperses the light, producing dispersed light 38. The dispersed light then enters imaging lenses 40a and 40b, which focuses light 42 onto a TDI detector 44.

As will be evident in FIG. 2, if the Figure depicts the imaging of object 24 over time, the object is shown at both a position 26 and a position 28 as it moves with fluid flow 22. As a consequence, images of object 24 will be produced on the detector at two discrete spatial positions 26' and 28', as indicated on the right side of FIG. 2. Alternatively, if FIG. 2 is depicting a single instant in time, positions 26 and 28 can represent the location of two separate objects, which are simultaneously imaged on the detector at positions 26' and 28'.

In regard to imaging system 20 and all other imaging systems illustrated herein, it will be understood that the lenses and other optical elements illustrated are shown only in a relatively simple form. Thus, the collection lens is illustrated as a compound lens comprising only collection lenses 32a and 32b. Lens elements of different designs, either simpler or more complex, could be used in constructing the imaging system to provide the desired optical performance, as will be understood by those of ordinary skill in the art. The actual lenses or optical elements used in the imaging system will depend upon the particular type of imaging application for which the imaging system will be employed.

In each of the embodiments of the present invention, it will be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion but either in different directions or at different rates.

The TDI detector that is used in the various embodiments of the present invention preferably comprises a rectangular charge-coupled device (CCD) that employs a specialized pixel read out algorithm, as explained below. Non-TDI CCD arrays are commonly used for 2-dimensional imaging in cameras. In a standard CCD array, photons that are incident on a pixel produce charges that are trapped in the pixel. The photon charges from each pixel are read out of the detector array by shifting the charges from one pixel to the next, and then onto an output capacitor, producing a voltage proportional to the charge. Between pixel readings, the capacitor is discharged and the process is repeated for every pixel on the chip. During the readout, the array must be shielded from any light exposure to prevent charge generation in the pixels that have not yet been read.

In one type of TDI detector 44, which comprises a CCD array, the CCD array remains exposed to the light as the pixels are read out. The readout occurs one row at a time from the top toward the bottom of the array. Once a first row is read out, the remaining rows are shifted by one pixel in the direction of the row that has just been read. If the object being imaged onto the array moves in synchrony with the motion of the pixels, light from the object is integrated for the duration of the TDI detector's total readout period without image blurring. The signal strength produced by a TDI detector will increase linearly with the integration period, which is proportional to the number of TDI rows, but the noise will increase only as the square root of the integration period, resulting in an overall increase in the signal-to-noise ratio by the square root of the number of rows. One TDI detector suitable for use in the present invention is a Dalsa Corp., Type IL-E2 image sensor, although other equivalent or better image sensors can alternatively be used. The Dalsa image sensor has 96 stages or rows, each comprising 512 pixels; other types of image sensors useable in the present invention may have different configurations of rows and columns or a non-rectilinear arrangement of pixels. The Dalsa sensor has approximately 96 times the sensitivity and nearly 10 times the signal-to-noise ratio of a standard CCD array. The extended integration time associated with TDI detection also serves to average out temporal and spatial illumination variations, increasing measurement consistency.

In imaging system 20 and in other embodiments of the present invention that employ a fluid flow to carry objects through the imaging system, a flow-through cuvette or a jet (not shown) contains the cells or other objects being analyzed. The velocity and cellular concentration of the fluid may be controlled using syringe pumps, gas pressure, or other pumping methods (not shown) to drive a sample solution through the system to match the pixel readout rate of the TDI detector. However, it should be understood that the readout rate of the TDI detector can be selectively controlled, as required, to match the motion of the sample solution.

Various optical magnifications can be used to achieve a desired resolution of the object that is being imaged on the light sensitive regions (pixels) of the TDI detector. It is contemplated that in most embodiments, the optical magnification will fall within a range of 1:1 to 50:1, providing a substantial range in the number of light sensitive regions on the TDI detector on which images of the object are formed, also depending of course, on the actual size of the object being imaged and its distance from the imaging system. It is envisioned that the present invention can have applications ranging from the analysis of cells and other microscopic objects to the imaging of stellar objects.

It should be emphasized that the present invention is not limited to CCD types of TDI detectors. Other types of TDI detectors, such as complementary metal oxide semiconductor (CMOS) and multi-channel plate imaging devices might also be used for the TDI detector in the present invention. It is important to understand that any pixellated device (i.e., having a multitude of light sensitive regions) in which a signal produced in response to radiation directed at the device can be caused to move through the device in a controlled fashion is suitable for use as the TDI detector in the present invention. Typically, the signal will move in synchrony with a moving image projected onto the device, thereby increasing the integration time for the image, without causing blurring. However, the motion of the signal can be selectively desynchronized from the motion of the radiation image, as required to achieve a desired affect.

Second Preferred Embodiment

Figure 4:
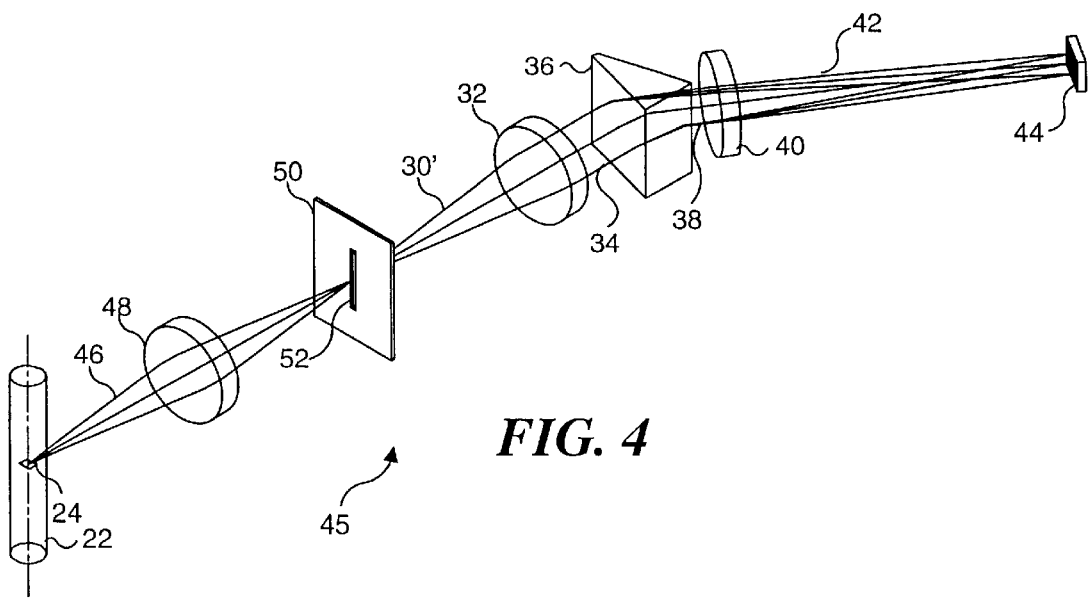
FIG. 4 is an isometric view of a confocal embodiment that includes a slit that is used for spatial filtering of extraneous light.

FIG. 4 illustrates an imaging system 45, which is a second preferred embodiment of the present invention and which is similar in many ways to imaging system 20. However, imaging system 45 is a confocal embodiment that includes a slit 52 that substantially prevents extraneous light from reaching TDI detector 44. In imaging system 45, light 46 from object 24 is focussed by an objective lens 48 onto a slit 52. Slit 52, as shown in FIG. 4, is sufficiently narrow to block light which is not focussed onto the slit by objective lens 48 from passing through the slit. Light 30' passes through the slit and is collected by collection lens 32 as discussed above, in regard to imaging system 20. Collected light 34 is spectrally dispersed by prism 36, and is imaged by imaging lens 40 onto TDI detector 44, also as discussed above. By excluding light other than that from object 24 from reaching TDI detector 44, the TDI detector produces an output signal that corresponds only to the actual images of the object, and the signal is not affected by the extraneous light, which has been excluded. If not excluded in this manner, the ambient light reaching TDI detector 44 might otherwise produce "noise" in the output signal from the TDI detector.

It should be noted that in the illustration of each of imaging systems 20 and 45, a light source has not been shown. These first two embodiments have been illustrated in their most general form to make clear that a separate light source is not required to produce an image of the object, if the object is luminescent, i.e., if the object produces light. However, many of the applications of the present invention will require that one or more light sources be used to provide light that is incident on the object being imaged. The location of the light sources substantially affects the interaction of the incident light with the object and the kind of information that can be obtained from the images on the TDI detector.

Figure 5:
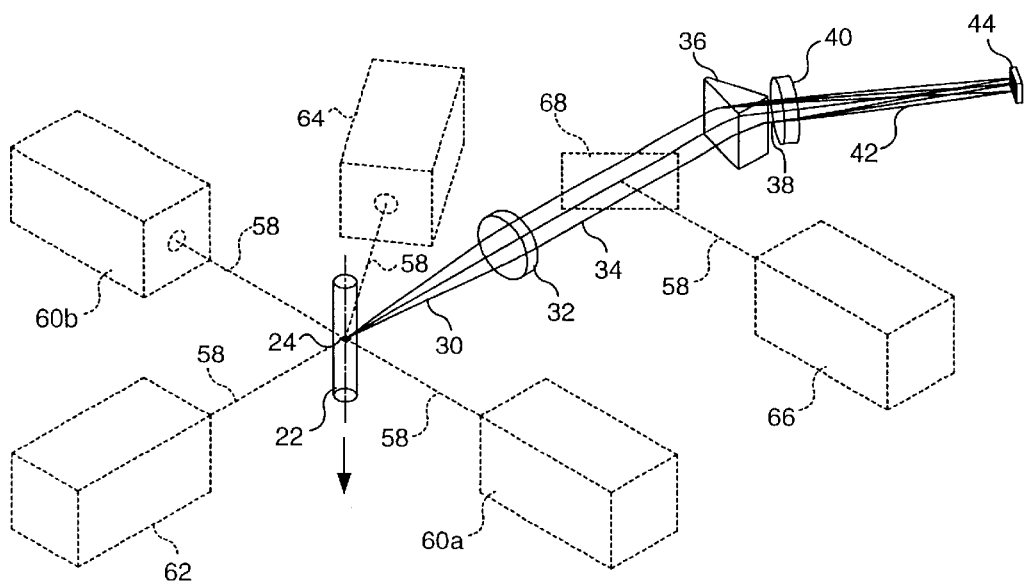
FIG. 5 is an isometric view showing different locations for a light source in connection with the first embodiment.

In FIG. 5, several different locations of light sources usable to provide light incident on object 24 are illustrated. It should be understood, however, that light sources can be located at many other positions besides those shown in FIG. 5. The location of each one or more light source employed will be dependent upon the kind of imaging of the object, and the kind of data for the object, to be derived from the signal produced by the TDI detector. For example, employing a light source 60a or a light source 60b, as shown in the Figure, will provide light 58 that is incident on object 24 and which is scattered from the object into the optical axis of collection lens 32. The optical axis of collection lens 32 is at about a 90° angle relative to the directions of the light incident upon object 24 from either light source 60a or 60b.

In contrast, a light source 62 is disposed so that light 58 emitted from the source travels toward the object in a direction that is generally aligned with the optical axis of collection lens 32, so that the image formed on TDI detector 44 will not include light absorbed by object 24. Light absorption characteristics of the object can thus be determined by illuminating the object using a light source 62.

A light source 64 is disposed to illuminate object 24 with light directed toward the object along a path that is approximately 30–45° off the optical axis of collection lens 32. This light 58, when incident on object 24 will be reflected (scattered) from object 24, and the reflected or scattered light will be imaged on TDI detector 44. A more directly reflected light is provided by an epi light source 66, disposed so as to direct its light 58 toward a partially reflective surface 68 that is disposed so that a portion of the light is reflected through collection lens 32 and onto object 24. The light reaching the object will be reflected from it back along the axis of collection lens 32 and will at least in part pass through partially reflective surface 68 to form an image of the object on TDI detector 44. Alternatively, a dichroic mirror may be employed instead of, and in the position of, partially reflective surface 68 to direct light from epi light source 66 to excite fluorescence or other stimulated emission from object 24. Emission from object 24 is then at least partially collected by collection lens 32 and passes through the dichroic mirror for spectral dispersion and detection by the TDI detector.

In addition to imaging an object with the light that is incident on it, a light source can also be used to stimulate emission of light from the object. For example, FISH probes that have been inserted into cells will fluoresce when excited by light, producing a corresponding characteristic emission spectra from any excited FISH probe that can be imaged on TDI detector 44. In FIG. 5, light sources 60a, 60b, 64, or 66 could alternatively be used for causing the excitation of FISH probes on object 24, enabling TDI detector 44 to image FISH spots produced by the FISH probes on the TDI detector at different locations as a result of the spectral dispersion of the light from the object that is provided by prism 36. The disposition of these FISH spots on the TDI detector surface will depend upon their emission spectra and their location in the object. Use of FISH probes in connection with producing images of FISH spots on the TDI detector with the present invention is discussed in greater detail below.

Each of the light sources illustrated in FIG. 5 produces light 58, which can either be coherent, non-coherent, broadband or narrowband light, depending upon the application of the imaging system desired. Thus, a tungsten filament light source can be used for applications in which a narrowband light source is not required. For applications such as stimulating the emission of fluorescence from FISH probes, narrowband laser light is preferred, since it also enables a spectrally-decomposed, non-distorted image of the object to be produced from light scattered by the object. This scattered light image will be separately resolved from the FISH spots produced on TDI detector 44, so long as the emission spectra of any FISH spots are at different wavelengths than the wavelength of the laser light. The light source can be either of the continuous wave (CW) or pulsed type. If a pulsed type illumination source is employed, the extended integration period associated with TDI detection can allow the integration of signal from multiple pulses. Furthermore, it is not necessary for the light to be pulsed in synchronization with the TDI detector.

Pulsed lasers offer several advantages over CW lasers as a light source in the present invention, including smaller size, higher efficiency, higher reliability, and the ability to deliver numerous wavelengths simultaneously. Another advantage of pulsed lasers is their ability to achieve saturating levels of fluorescence excitation of fluorescent probes used in cells. Fluorescence saturation occurs when the number of photons encountering a fluorescent molecule exceeds its absorption capacity. Saturating excitation produced by a pulsed laser is inherently less noisy than unsaturating CW laser excitation because variations in pulse-to-pulse excitation intensity have little effect on the fluorescence emission intensity.

Prism 36 in the imaging systems discussed above can be replaced with a diffraction grating, since either is capable of spectrally dispersing the optical signals from the cells over the pixels of the TDI detector. In addition to providing useful data from a cell or other object, spectral dispersion can be used to reduce measurement noise. In cases where the light source wavelength differs from the emission spectra of the fluorescent probes, the light from the source that is scattered into the collection system is spatially isolated from the fluorescence signals. If the light source wavelength overlaps the emission spectra of the fluorescent probes, the pixels of the TDI detector in which light of the wavelength of the source falls can be isolated from those pixels on which the remaining fluorescence signals fall. Further, by dispersing the fluorescence signals over multiple pixels, the overall dynamic range of the imaging system is increased.

Third Preferred Embodiment

Figure 6:
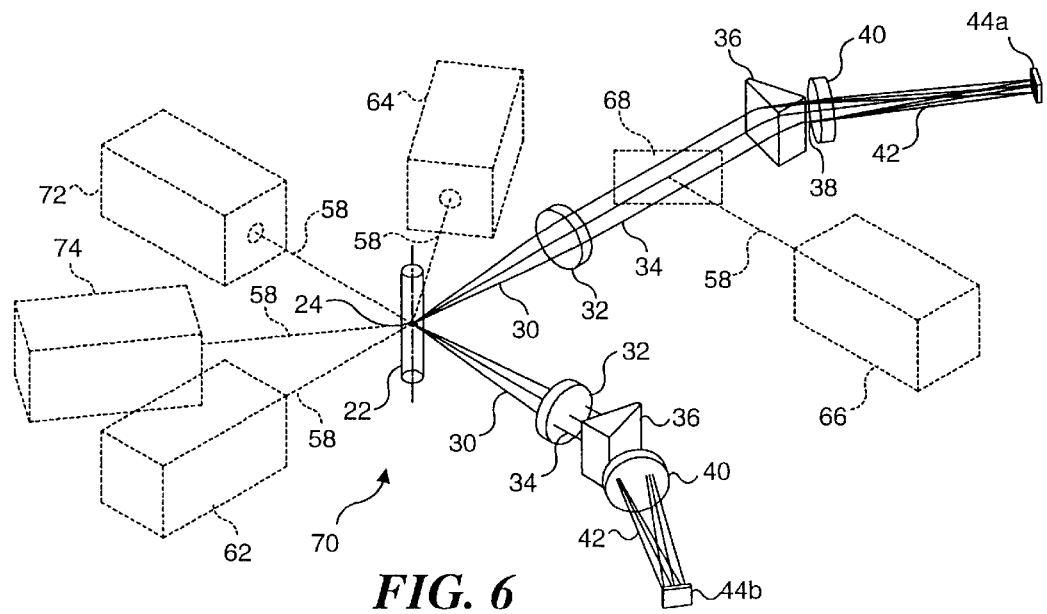
FIG. 6 is an alternative to the first embodiment in which a second set of imaging components and TDI detector is included for monitoring light from a particle, to avoid interference between FISH probes, and showing alternative locations for light sources.

A third preferred embodiment is a stereoscopic arrangement 70 of the first preferred embodiment, as illustrated in FIG. 6. This arrangement allows the imaging of the object from two different directions in order to distinguish features that would otherwise overlap when viewed from a single direction. While the third preferred embodiment can be employed for objects on moving substrates such as microscope slides, it is particularly useful for analyzing multi-component objects in solution, such as cells containing FISH probes. Such probes appear as point sources of light anywhere within the cell's three-dimensional nucleus. In some cases, two or more FISH probes may appear in an overlapping relationship along the optical axis of the imaging system. In such cases, one of the FISH probes may obscure the others, making it difficult to determine the number of probes present in the cell. This is a key factor in the determination of genetic abnormalities such as trisomy 21, otherwise known as Down syndrome. Single-perspective systems may address this problem by "panning through" the object along the optical axis to acquire multiple image planes in the object. While this method may be effective, it requires a significant amount of time to collect multiple images and cannot be readily applied to a cell in flow. The stereoscopic imaging system 70 in FIG. 6 includes two TDI detectors 44a and 44b, and their associated optical components, as discussed above in connection with imaging system 20.

By positioning the optical axes of collection lenses 32 for the two TDI detectors so that they are spaced apart, for example, by 90°, it is possible to separately resolve the FISH spots imaged from two or more FISH probes on at least one of TDI detectors 44a or 44b. If two or more FISH probes overlap in regard to the image produced on one of the detectors, they will be separately resolved in the spectrally dispersed images produced on the other TDI detector. Further, the use of two TDI detectors in imaging system 70 in what might be referred to as a "stereo or three-dimensional configuration" allows flexibility in the configuration of each leg of the system, including parameters such as the relative TDI readout rates, axial orientations, inclinations, focal plane positions and magnification. Multiple cells or other objects may be imaged onto each detector simultaneously in the vertical direction. Since the objects may move in synchronicity with the signal on the TDI, no gate or shutter is required to prevent blurring of the image. As previously noted, the present invention can use a pulsed or CW light source without need for a trigger mechanism to time a pulse coincident with particle arrival in the field of view. If a pulsed light source is used, the extended field of view in the axis of motion associated with TDI detection allows the cell or object in motion to be illuminated by multiple pulses during its traversal. In contrast to a frame-based imaging apparatus, a TDI system can produce a single unblurred image of the object that integrates the signal from multiple pulses. When a CW light source is used, the signal generated by the object will be collected throughout the entire traversal of the object through the field of view, as opposed to only a small segment in time when a shutter is open. Therefore, the amount of signal collected and imaged on the detector in the present invention is substantially greater than that of the prior art frame-based imaging systems. Consequently, the present invention can operate at very high throughput rates with excellent signal-to-noise ratio.

Also illustrated in FIG. 6 are several exemplary positions for light sources, which are useful for different purposes in connection with the imaging system illustrated therein. In connection with TDI detector 44a, light source 62 provides illumination of object 24 from a direction so that absorption characteristics of the object can be determined from the image produced on the TDI detector. At the same time, light provided by light source 62 that is scattered from object 24 can be used to produce a scatter image and spectrally dispersed images on TDI detector 44b. Light source 74 can be employed to produce spectrally dispersed and scattered images on both TDI detectors 44a and 44b. If light sources 62 and 72 are of different wavelengths and an appropriate filter is provided to block the wavelength from the light source aligned with the optical axis of the respective collections lenses 32, these two light sources can be used for producing scattered light from the object. For example, suppose light source 72 produces light of a wavelength A that scatters from object 24 and is directed toward TDI detector 44a. By including a filter (not shown) that blocks wavelength B produced by light source 62, the light at wavelength B will not directly affect the images produced on TDI detector 44a. Similarly, the light from light source 72 would be blocked with an appropriate filter (not shown) so that it does not interfere with the imaging of light produced by light source 62 that is scattered from object 24 onto TDI detector 44b.

Epi light source 66 is also illustrated for use in producing images on TDI detector 44a in conjunction with partial reflector 68. Light source 64 can be used to generate reflected light to produce images on TDI detector 44a, while scattered light from this source is directed toward TDI detector 44b. These and other possible locations of light sources will be apparent to those of ordinary skill in the art, as appropriate for providing the incident light on the object needed to achieve imaging, depending upon the particular application and information about the object that is desired.

Imaging Slide or Object Carried by Slide

Figure 7:
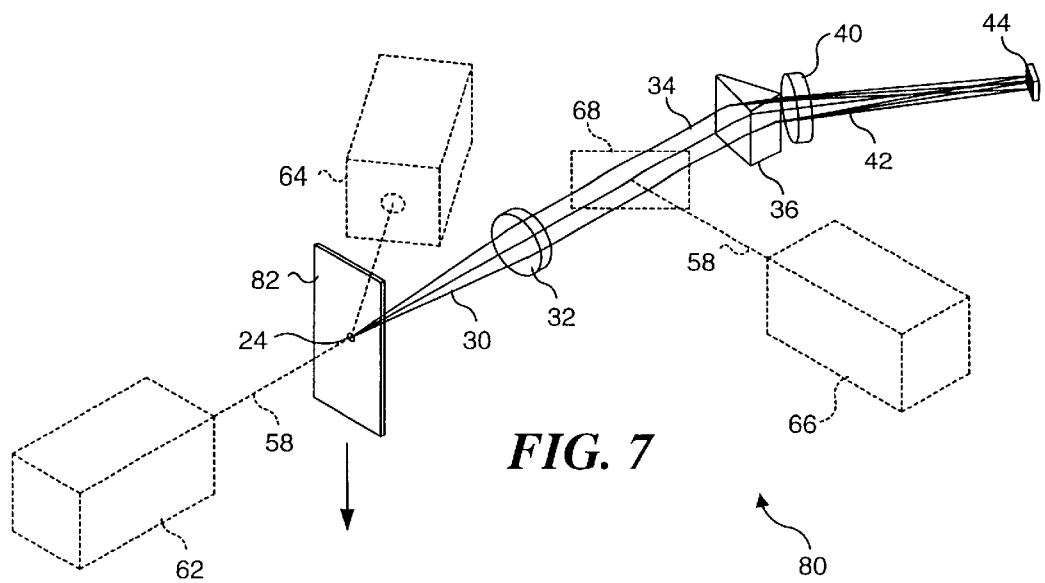
FIG. 7 is an isometric view of an embodiment in which an object is supported by or comprises a slide that moves past a collection lens, showing different locations for a light source.

Turning now to FIG. 7, an imaging system 80 is illustrated that is similar to imaging system 20, except that it is used for imaging object 24 on a slide 82. Object 24 is supported by slide 82 and the slide moves relative to the imaging system as shown in FIG. 7. Alternatively, slide 82 may be the object that is imaged. The object may be a semiconductor wafer, paper, or other object of interest since the object may be imaged using reflected incident light.

To provide light incident on either slide 82 or object 24 that is supported thereby, a light source placed at one of several different locations can be employed. Exemplary light sources 62, 64, and 66 illustrate some of the locations at which light sources useful in this embodiment may be disposed. Light 58 emitted by any of the light sources can be either coherent or non-coherent light, pulsed or CW, and can be directed through slide 82 (if it is transparent) from light source 62 or can be reflected from the object or slide, if light sources 64 or 66 are employed. As noted previously, epi light source 66 illuminates the object in connection with a partially reflective surface 68.

Fourth Preferred Embodiment

Figure 8A:
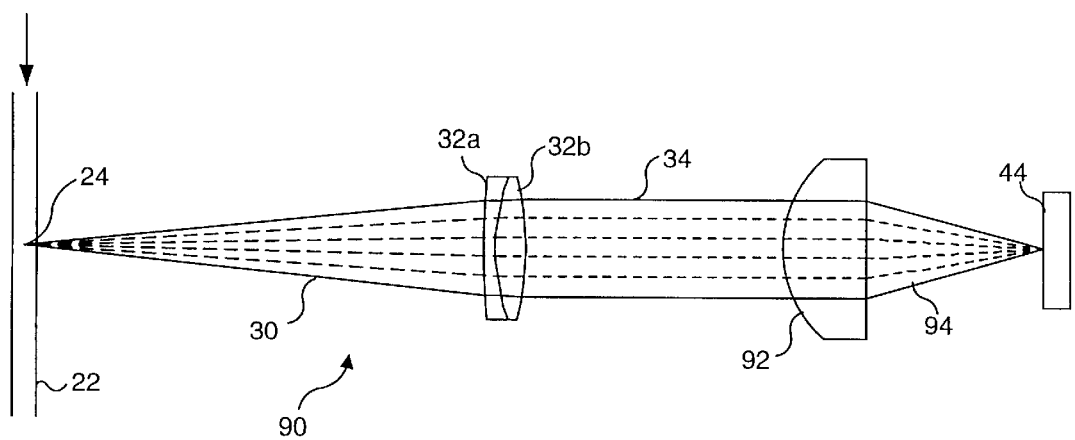
FIGS. 8A and 8B are respectively a plan view and a side elevational view of an alternative to the embodiment of FIG. 7 that is used to produce a scattered pattern on the TDI detector.
Figure 8B:
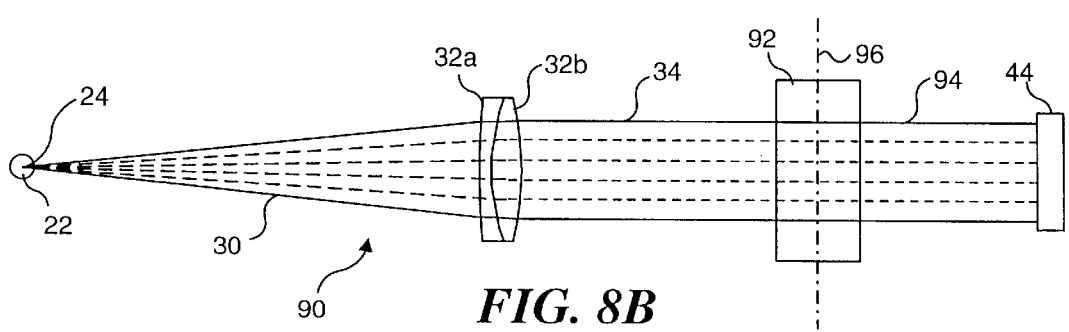

FIGS. 8A and 8B show two different views of a fourth preferred embodiment, which is an imaging system 90 that produces a scattered pattern image of object 24 on TDI detector 44. Light 30 from object 24 passes through collection lenses 32a and 32b, and collected light 34 is directed onto a cylindrical lens 92, as in the previous embodiments. Cylindrical lens 92 focuses light 94 on TDI detector 44, generally along a line that is aligned with a central axis 96 of cylindrical lens 92. Central axis 96 is shown in FIG. 8B, and it will be apparent that it is orthogonal to the direction in which object 24 moves through the imaging system. As object 24 moves downwardly, relative to its disposition as shown in FIG. 8A, the focus of cylindrical lens 92 on TDI detector 44 moves upwardly. Cylindrical lens 92 thus distributes an image of the object along a row or rows of the light sensitive regions or pixels of TDI detector 44.

Fifth Preferred Embodiment

Figure 9:
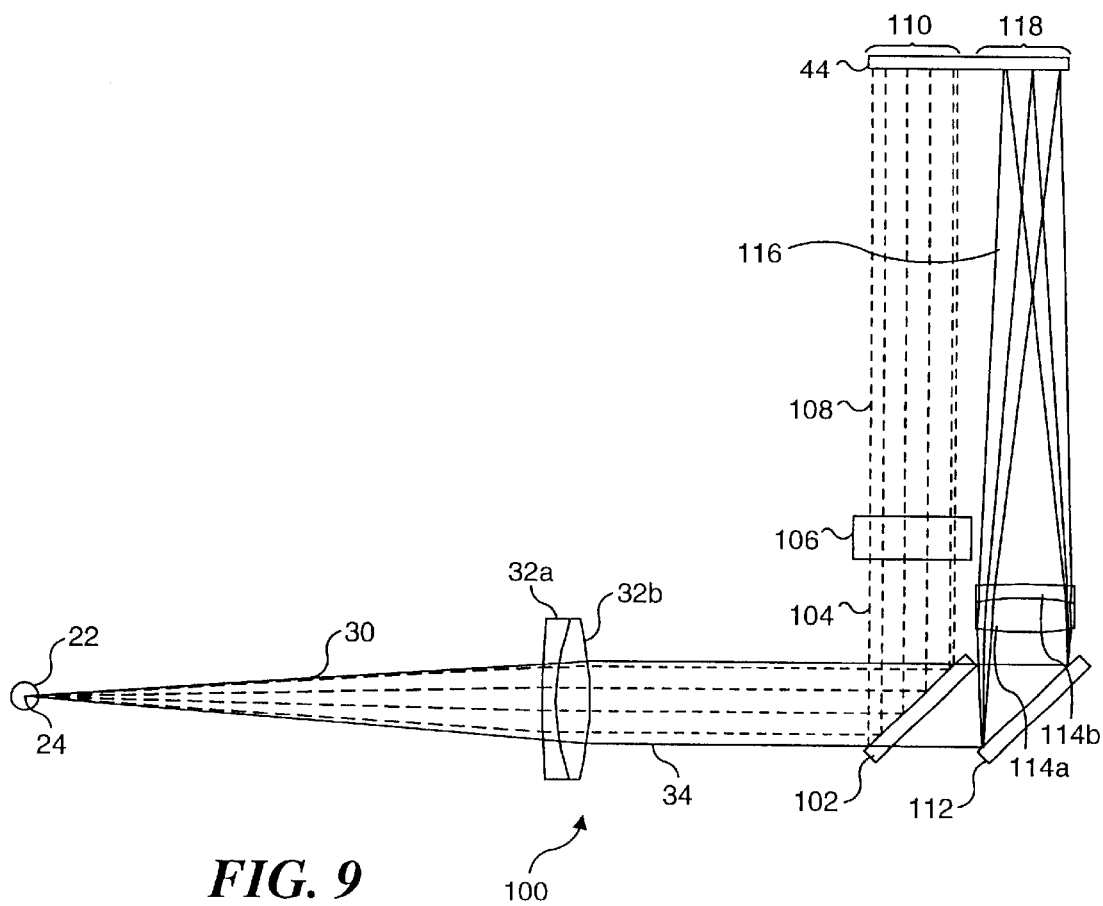
FIG. 9 is a plan view of yet a further embodiment in which light forming a scatter patterned image and spectrally dispersed light from the object are imaged on separate portions of a TDI detector.

Referring now to FIG. 9, an illustration of a fifth preferred embodiment is provided of an imaging system 100 that produces both a scattered pattern image and a spectrally dispersed image of object 24 on TDI detector 44. In imaging system 100, light 30 from object 24 passes through collections lenses 32a and 32b, which produce infinitely focussed light 34 directed toward a dichroic filter 102. Dichroic filter 102 reflects light of a specific wavelength, e.g., the wavelength of a light source (not shown) that is incident upon object 24. Light of any other wavelength is transmitted through dichroic filter 102 toward a diffraction grating 112. Diffraction grating 112 spectrally disperses the light transmitted through dichroic filter 102, which typically would be light produced by the fluorescence of FISH probes on object 24, so that a plurality of FISH spots corresponding to the number of different FISH probes and objects being imaged are produced on TDI detector 44.

Light 104, which is reflected from dichroic filter 102 is transmitted into cylindrical lens 106 and is focussed along a line as a scattered pattern image in a region 110 on the TDI detector. The spectrally dispersed images of FISH spots or other aspects of object 24 having wavelengths different than that reflected by dichroic filter 102 are imaged as light 116 by imaging lenses 114a and 114b onto a region 118 of the TDI detector. Thus, signals corresponding to the scattered pattern image and the spectrally dispersed images are both produced by TDI detector 44.

Sixth Preferred Embodiment

Figure 10:
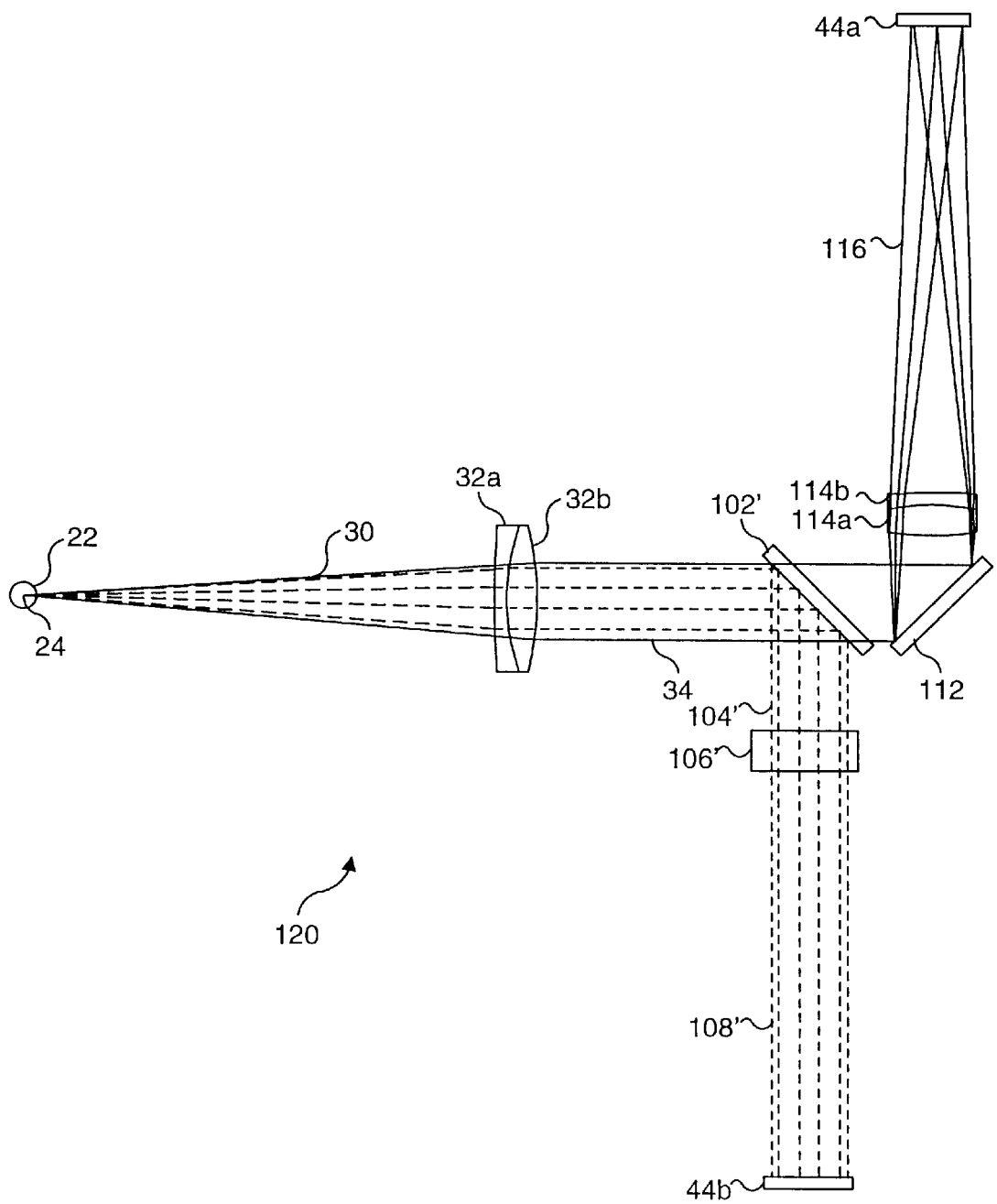
FIG. 10 is a plan view of a still further embodiment in which light forming a scatter patterned image and spectrally dispersed light from the object are imaged by two different TDI detectors.

A sixth preferred embodiment, as illustrated in FIG. 10, is an imaging system 120 that is slightly different than the preceding fifth embodiment, since a dichroic filter 102' is employed that is angled in a different direction, toward a second TDI detector 44b. A dispersed pattern image represented by light 108' is produced by a cylindrical lens 106' in this embodiment. Just as in imaging system 100, light transmitted through dichroic filter 102' is focussed onto TDI detector 44a. Aside from using two separate TDI detectors that are disposed at different sides of the imaging system, imaging system 120 is substantially identical in operation to imaging system 100. However, just as in the third preferred embodiment, the use of two separate TDI detectors allows flexibility in the configuration of each leg of the system, including parameters such as the relative TDI readout rates, axial orientations, inclinations, focal plane positions, and magnification. It should also be noted that imaging system 100 could be constructed to include two separate TDI detectors instead of a single TDI detector, if desired.

Processing of Spectrally Dispersed Images on TDI Detector

When used for cell analysis, the present invention provides substantial utility in resolving FISH spots on the TDI detector, even when the FISH probes are disposed in spatially close relationship within the cell. When spectral imaging occurs in the present invention, the spatial distribution of light in the object is convolved with the spectral distribution of that light to produce the image of the object at the TDI detector. This convolution can result in blurring in the dispersion axis, depending on the spectral bandwidth of the light. Narrow spectral bandwidths will result in little or no blurring depending on the spectral resolution of the system. In the present invention, it is contemplated that the spectral resolution will be approximately 3 nm per pixel, with a spatial resolution in object space of approximately 1 micron. However, the spatial and spectral resolution can be adjusted to match the requirements of the particular application.

Figure 11:
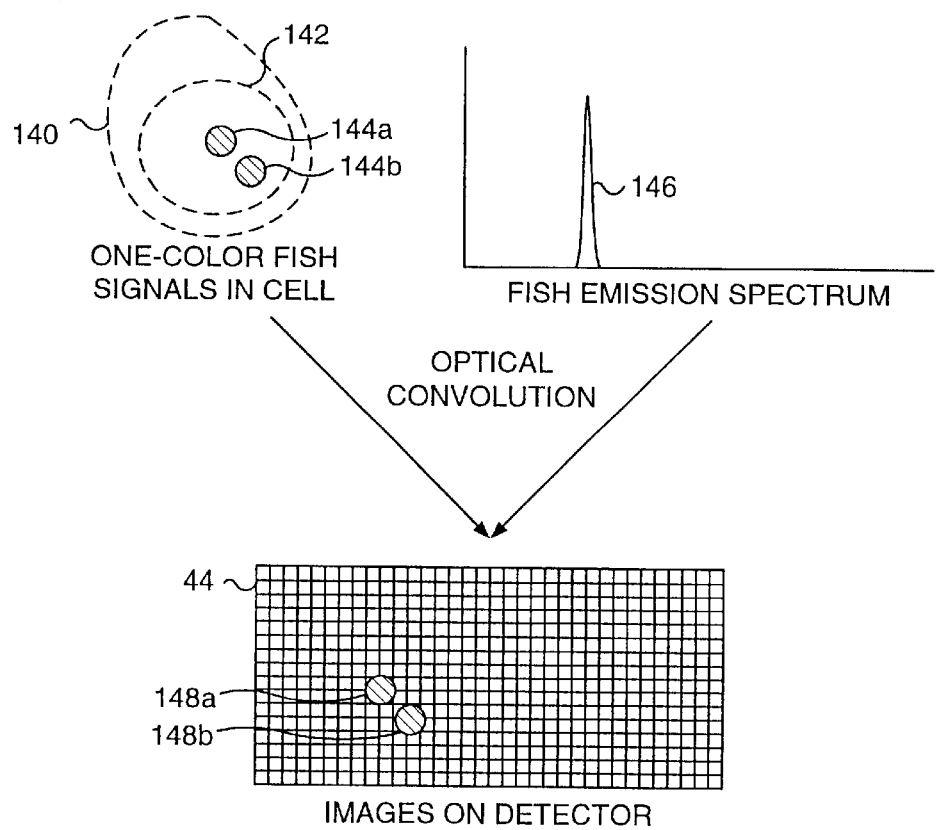
FIG. 11 is a schematic diagram illustrating the optical convolution of a narrow FISH emission spectrum by the present invention, to resolve two FISH probes in a cell.

FIG. 11 illustrates the present invention with a spectral resolution of approximately 10 nm per pixel and a spatial resolution of approximately 0.5 microns. This Figure further illustrates how the present invention is used to image a cell 140 having a nucleus 142 in which are disposed two FISH probes 144a and 144b having the same emission spectrum. In FIG. 11, the emission spectrum 146 of the FISH probes 144a and 144b is approximately 10 nm in width, such as would be produced by "quantum dots" or a narrow-band fluorescent dye. The optical convolution of the narrow bandwidth spectrum results in minimal blurring of FISH spots 148a and 148b, enabling them to be readily resolved on TDI detector 44.

Figure 12:
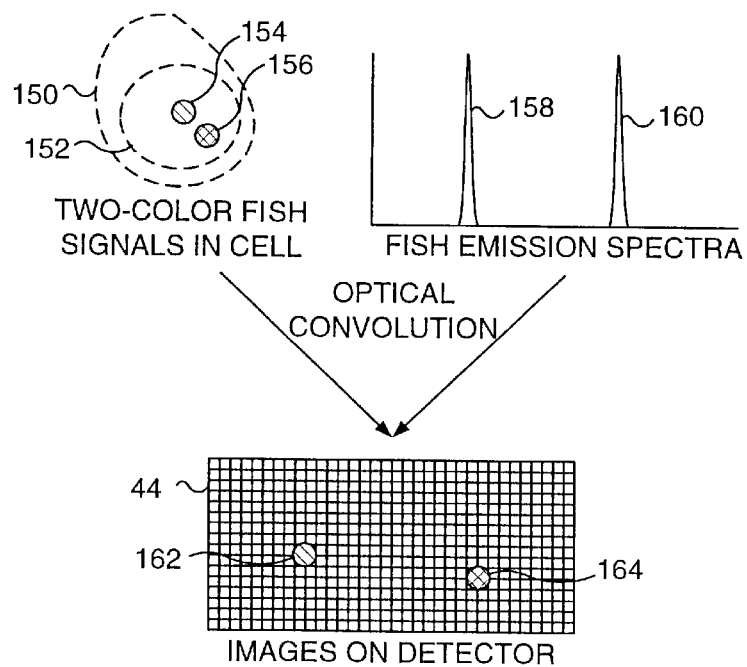
FIG. 12 is a schematic diagram showing the optical convolution of two different colors of narrow FISH emission spectra, to resolve the image of the FISH probes on the TDI detector.

In FIG. 12, a cell 150 is illustrated having a nucleus 152 in which are disposed FISH probes 154 and 156 having different emission spectra. FISH probes are designed so that different emission spectra correspond to different DNA sequences. Each of the emission spectra of FISH probes 154 and 156 are relatively narrow, as indicated by wavebands 158 and 160, and therefore, as in FIG. 11, minimal blurring occurs in FISH spots 162 and 164. Furthermore, the spectral dispersion of the present invention, which maps wavelength into lateral position on TDI detector 44, produces a relatively wide physical displacement of FISH spots 162 and 164, despite the close proximity of FISH probes 154 and 156 in the cell. Taken together, FIGS. 11 and 12 illustrate how the present invention discriminates FISH probes of the same or different color, thereby enabling the simultaneous enumeration of numerous genetic traits. Those skilled in the art can appreciate that the present invention is well suited to the requirements of fetal cell analysis, where there may be ten or more probes of different colors present in the cell at one time. Further, those skilled in the art will appreciate that the present invention is not limited to the analysis of fetal cells using FISH probes.

Figure 13:
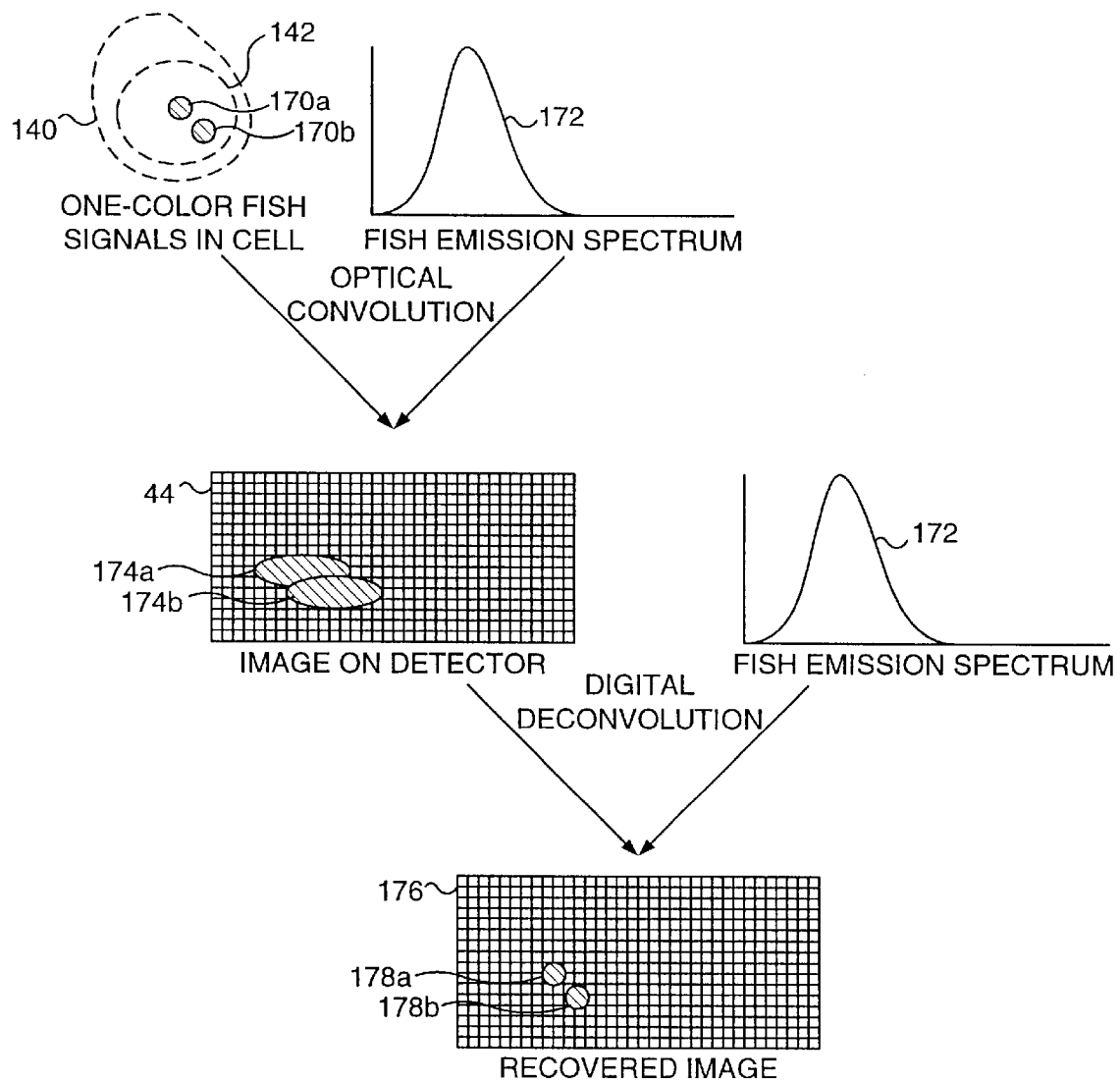
FIG. 13 is a schematic diagram illustrating how for a wider FISH emission spectrum, a deconvolution is provided by the present invention to resolve the image of two FISH probes of a single color.
Figure 14:
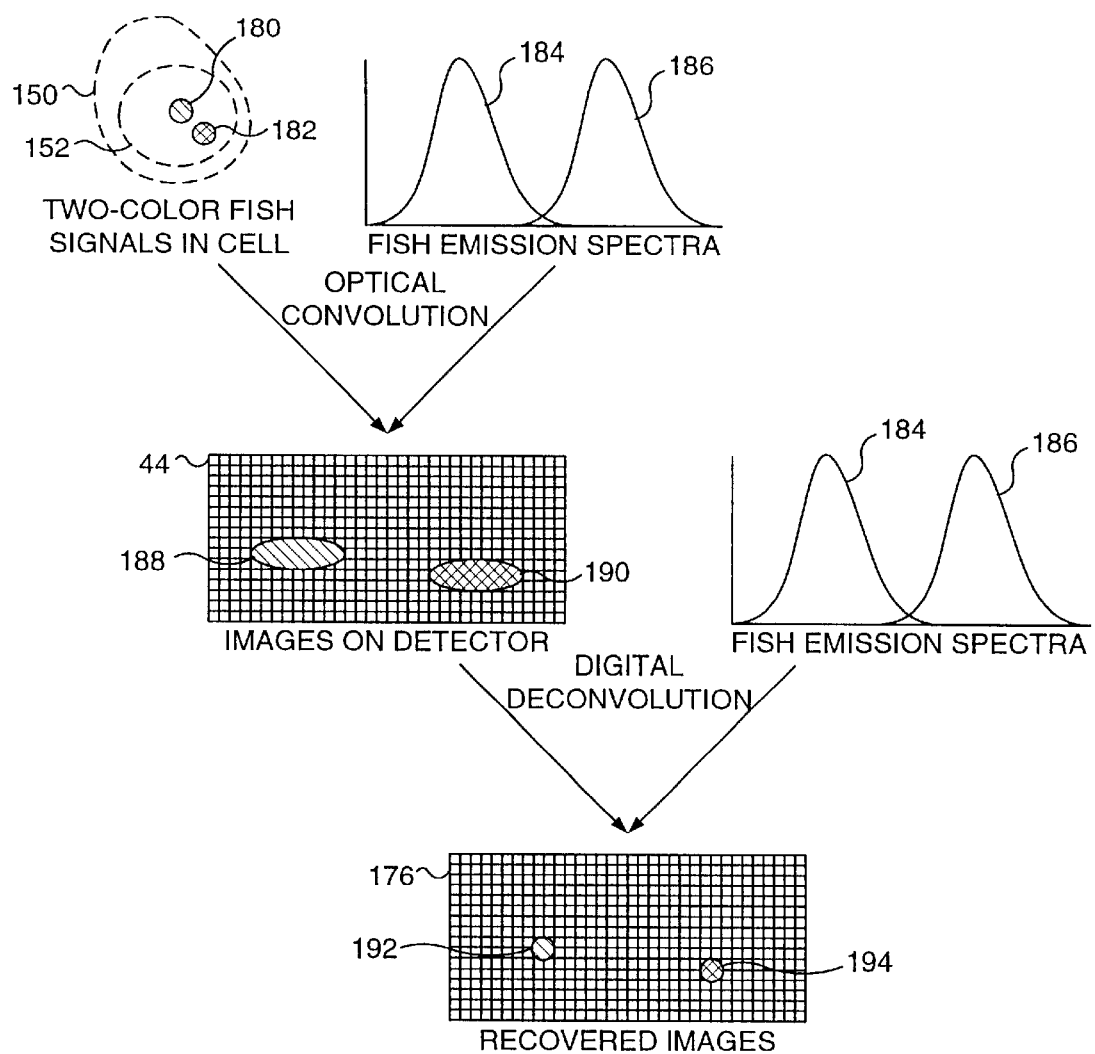
FIG. 14 is a schematic diagram showing the deconvolution of two color FISH spectra that are relatively wide, to resolve the image of the FISH probes.

FIGS. 13 and 14 illustrate that the present invention can also be used with light of wide spectral bandwidth. In this case an additional signal processing step is performed to correct for lateral blurring due to the wide emission spectra. In FIG. 13, a cell 140 having a nucleus 142 is shown, and FISH probes 170a and 170b having a common emission spectrum are disposed in the nucleus. FISH probes 170a and 170b are characterized by producing a relatively wide emission spectrum 172. When optically convolved by the spectral dispersion provided by the present invention, FISH spots 174a and 174b are produced on TDI detector 44, but their images are laterally blurred across TDI detector 44, as a result of their relatively wide emission spectrum. To more clearly resolve the separation of FISH spots 174a and 174b, a deconvolution is carried out on the signal produced by TDI detector 44, with the known FISH emission spectrum, thereby producing accurate FISH spot representations 178a and 178b on a display 176. The deconvolution step enhances the ability to enumerate the number of FISH spots.

FIG. 14 illustrates a corresponding relationship between FISH probes 180 and 182, which are disposed within a nucleus 152 of a cell 150. FISH probes 180 and 182 are characterized by each producing relatively wide band emission spectra 184 and 186, as shown in the Figure. Optical convolution of the fluorescence emitted by the FISH probes, which are spectrally dispersed, produces FISH spots 188 and 190 on TDI detector 44. Again, by deconvolving the known FISH emission spectra with the signal produced by TDI detector 44, the corresponding images shown on display 176 of FISH spots 192 and 194 are recovered. Again, the spectral dispersion of the present invention, which maps wavelength into lateral position on TDI detector 44, produces a relatively wide physical displacement of FISH spots 192 and 194, despite the close proximity of FISH probes 180 and 182 in the cell. In this manner, it is possible to resolve these images of FISH spots produced by FISH probes having different and relatively wide emission spectra.

Figure 15:
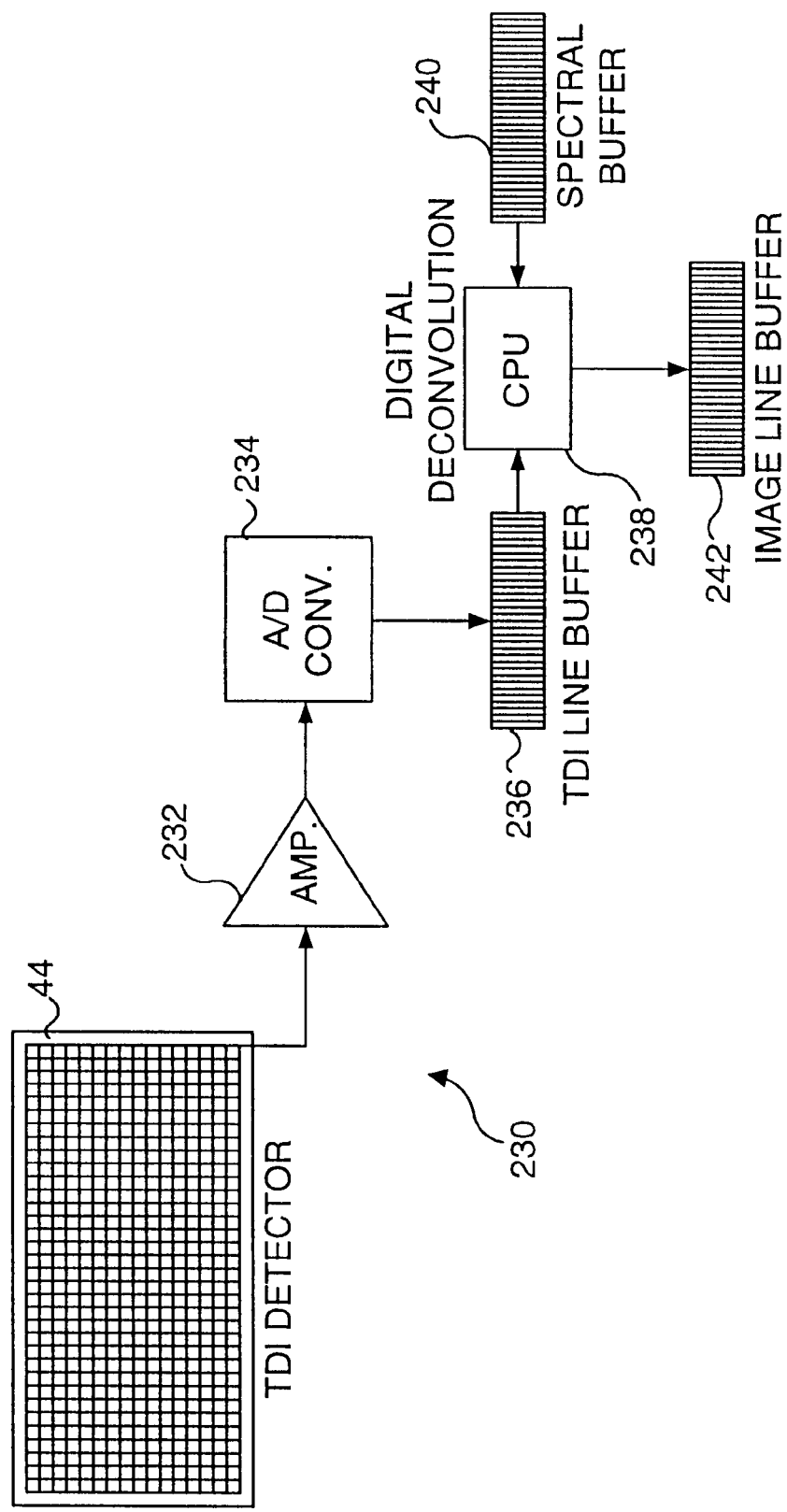
FIG. 15 is a schematic block diagram of the system used to process the signal produced by a TDI detector in the present invention.

A system 230 for analyzing the signal produced by TDI detector 44 and performing the deconvolution steps described above is illustrated in FIG. 15. In this Figure, the signal from TDI detector 44 is applied to an amplifier 232, which buffers the signal and amplifies it to achieve a level required by an analog to digital (A-D) converter 234. This A-D converter converts the analog signal from amplifier 232 into a digital signal that is input into a TDI line buffer 236. TDI line buffer 236 temporarily stores the digital signal until it can be processed by a CPU 238. To carry out the deconvolution noted above, a spectral buffer 240 is loaded with the known emission spectrum for each of the FISH probes being used so that their emission spectra can be deconvolved with the signal stored in TDI line buffer 236. CPU 238 is a high speed processor programmed to carry out the deconvolution and other analysis procedures, enabling the identification of desired characteristics or parameters of the object being imaged. The output from CPU 238 is temporarily stored in an image line buffer 242 that enables the image to be displayed or otherwise recorded for later analysis.

Figure 16:
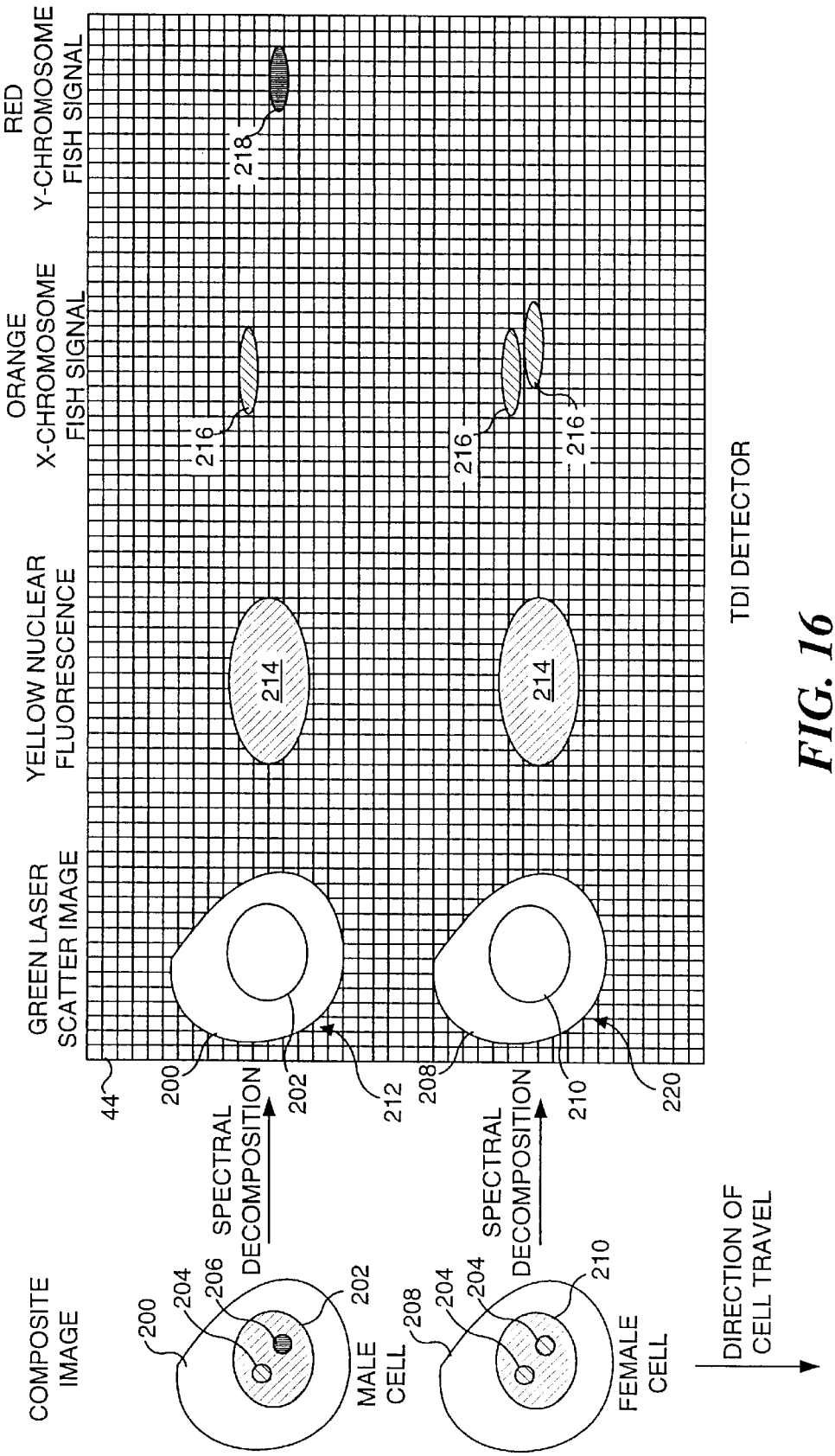
FIG. 16 is a schematic diagram illustrating how the present invention is used to determine whether a cell is from a male or female.

FIG. 16 illustrates a practical application of the present invention for identifying a male cell 200 and a female cell 208 and for producing their corresponding scatter images 212 and 220. Male cell 200 includes a nucleus 202 that has been stained with a yellow fluorescent dye. In addition, a FISH probe 204 produces a fluorescent orange emission, indicating the presence of an X-chromosome in the nucleus, while a FISH probe 206 produces red fluorescence emission, indicating the presence of a Y-chromosome. Spectral decomposition of the fluorescence emissions from male cell 200, when the cell is illuminated with light from a green laser, results in a series of images on TDI detector 44, separated as a function of the wavelength of the light that is imaged. Laser light that is incident on the cells has an extremely narrow waveband, and image 212 of male cell 200 produced by laser scatter is only slightly convoluted by the spectral decomposition process. Green laser scatter image 212 of cell 200 and its nucleus 202 appear on the left side of the TDI detector, while a fluorescent spot 214 corresponding to the yellow fluorescence emitted by nucleus 202 appears in the next few columns on the TDI detector. Furthermore, as a function of the different wavelengths of the fluorescence emitted by FISH probes 204 and 206, FISH spots 216 and 218 appear at locations spaced apart on the detector, but slightly blurred across the columns of TDI detector 44 due to the widths of their respective emission spectra. By analyzing the signals produced by the TDI detector, the FISH probes responsive to X and Y chromosomes are detected, enabling the user to determine that cell 200 is a male cell, since it includes both the X and Y chromosome. Similarly, female cell 208, when spectrally decomposed, also includes the characteristic yellow fluorescence of nucleus 210, but unlike the male cell, includes two FISH spots 216 corresponding to FISH probes 204, which indicates the presence of two X-chromosomes. Because TDI detector 44 also distinguishes the spatial position of male cell 200 and female cell 208, the corresponding spectral decompositions for these cells are readily separately resolved as both cells pass through the imaging system in the direction indicated by the arrow to the lower left of FIG. 16. Again, it should be noted that a deconvolution can be applied to the signal produced by TDI detector 44 to provide better resolution of the corresponding FISH spots that are illustrated.

Non-Distorting Spectral Dispersion Systems

Figure 17:
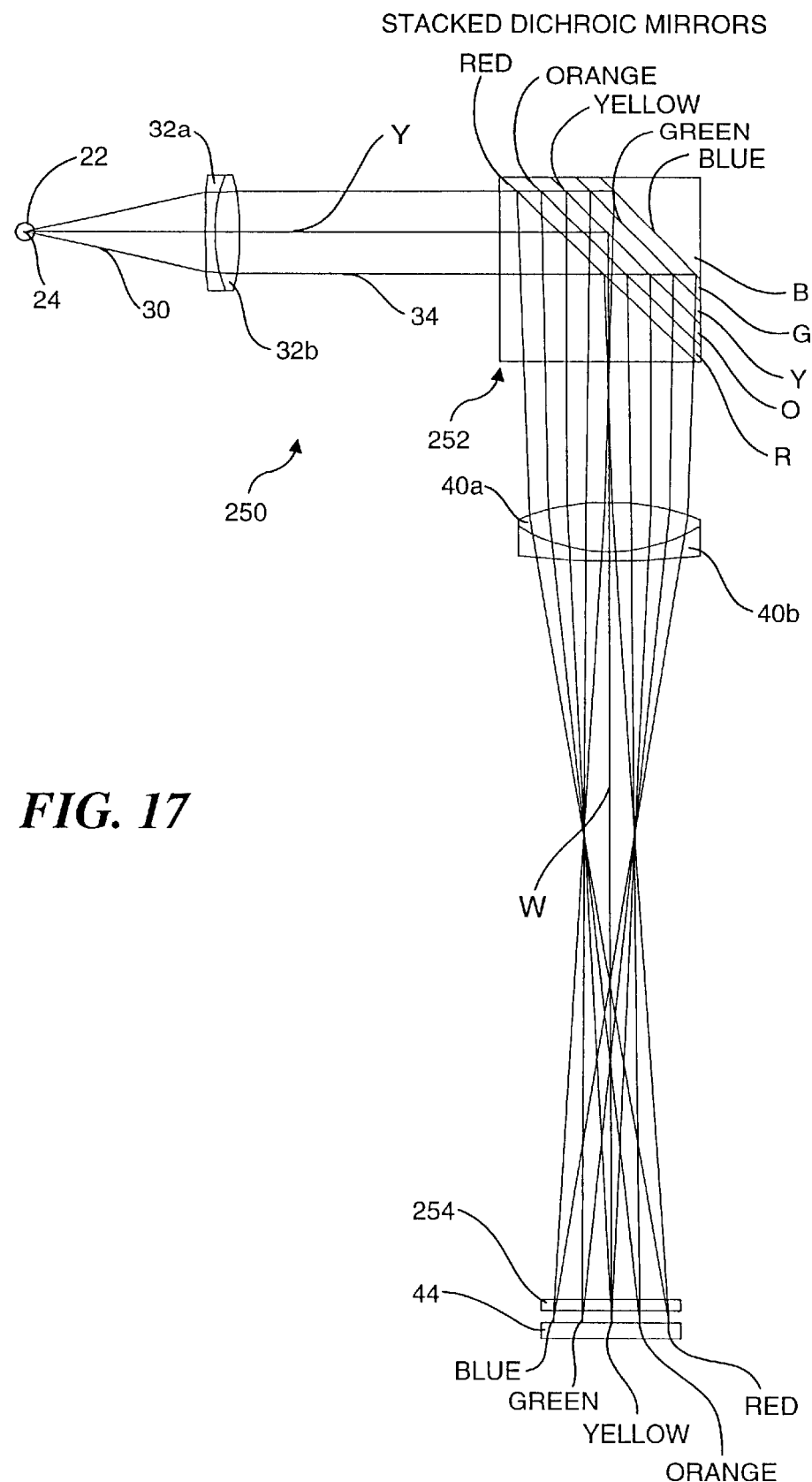
FIG. 17 is a plan view of an alternate embodiment that employs a spectral dispersion component comprising a plurality of stacked dichroic filters employed to spectrally separate the light.

The present invention can be provided with a spectral dispersion filter assembly that does not convolve the image with the emission spectra of the light forming the image, thereby eliminating the need for deconvolution of the emission spectra from the image. FIG. 17 illustrates a seventh preferred embodiment of the invention corresponding to such a non-distorting spectral dispersion system 250 that employs a five color stacked wedge spectral dispersing filter assembly 252. This seventh embodiment is substantially similar to the embodiment shown in FIGS. 1, 2, and 3, except that spectral dispersing prism element 36 (of FIGS. 1, 2 and 3) is replaced by spectral dispersing filter assembly 252. The spectral dispersing filter assembly splits the light into a plurality of light beams having different bandwidths. Each light beam thus produced is directed at a different nominal angle so as to fall upon a different region of TDI detector 44. The nominal angular separation between each bandwidth produced by the spectral dispersing filter assembly 252 exceeds the field angle of the imaging system in object space thereby preventing overlap of the field images of various bandwidths on the detector.

Figure 18:
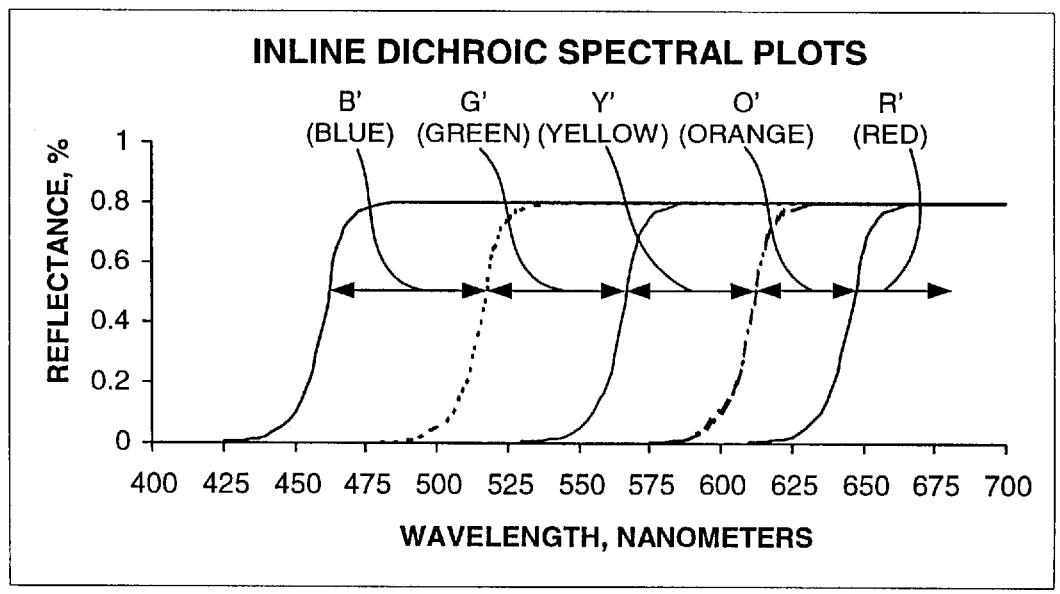
FIG. 18 is an X-Y plot of several typical passbands for the dichroic filters employed in the embodiment shown in FIG. 17.

Spectral dispersing filter assembly 252 comprises a plurality of stacked dichroic wedge filters, including a red dichroic filter R, an orange dichroic filter O, a yellow dichroic filter Y, a green dichroic filter G, and a blue dichroic filter B. Red dichroic filter R is placed in the path of collected light 34, oriented at an angle of approximately 44.0° relative to an optic axis 253 of collection lenses 32a and 32b. Light of red wavelengths and above, i.e., >640 nm, is reflected from the surface of red dichroic filter R at a nominal angle of 1°, measured counter-clockwise from a vertical optic axis 257. Example spectral reflectance characteristics R' of red dichroic filter R are plotted in FIG. 18, along with example spectral reflectance characteristics corresponding to the other dichroic filters used in spectral dispersing filter assembly 252. In FIG. 18, O' indicates the spectral reflectance characteristics of orange dichroic filter O, Y' indicates the spectral reflectance characteristics of yellow dichroic filter Y, etc. The light reflected by red dichroic filter R leaves spectral dispersing filter assembly 252 and passes through imaging lenses 40a and 40b, which cause the light to be imaged onto a red light receiving region of TDI detector 44, which is disposed toward the right end of the TDI detector, as shown in FIG. 17.

Orange dichroic filter O is disposed a short distance behind red dichroic filter R and is oriented at an angle of 44.5 degrees with respect to optic axis 253. Light of orange wavelengths and greater, i.e., >610 nm, is reflected by orange dichroic filter O at a nominal angle of 0.5° with respect to vertical optic axis 257. Because the portion of collected light 34 comprising wavelengths longer than 640 nm was already reflected by red dichroic filter R, the light reflected from the surface of orange dichroic filter O is effectively bandpassed in the orange colored region between 610 nm and 640 nm. This light travels at a nominal angle of 0.5° from vertical optic axis 257, and is imaged by imaging lenses 40a and 40b so as to fall onto an orange light receiving region disposed toward the right hand side of TDI detector 44 between a center region of the TDI detector and the red light receiving region, again as shown in FIG. 17.

Yellow dichroic filter Y is disposed a short distance behind orange dichroic filter O and is oriented at an angle of 45° with respect to optic axis 253. Light of yellow wavelengths, i.e., 560 nm and longer, is reflected from yellow dichroic filter Y at a nominal angle of 0.0° with respect to vertical optic axis 257. Wavelengths of light reflected by yellow dichroic filter Y are effectively bandpassed in the yellow region between 560 nm and 610 nm and are imaged by imaging lenses 40a and 40b near vertical optic axis 257 so as to fall on a yellow light receiving region toward the center of TDI detector 44.

In a manner similar to dichroic filters R, O, and Y, dichroic filters G and B are configured and oriented so as to image green and blue light wavebands onto respective green and blue light receiving regions of TDI detector 44, which are disposed toward the left-hand side of the TDI detector. By stacking the dichroic filters at different predefined angles, spectral dispersing filter assembly 252 collectively works to focus light within predefined wavebands of the light spectrum onto predefined regions of TDI detector 44. Those of ordinary skill in the art will appreciate that the filters used in the spectral dispersing filter assembly 252 may have spectral characteristics that differ from those described above and in FIG. 18. Further, the spectral characteristics may be arbitrary and not limited to dichroic in order to achieve the desired dispersion characteristics.

The wedge shape of the dichroic filters in the preceding discussion allows the filters to be placed in near contact, in contact or possibly cemented together to form the spectral dispersing filter assembly 252. The angle of the wedge shape fabricated into the substrate for the dichroic filter allows easy assembly of the spectral dispersing filter assembly 252, forming a monolithic structure in which the wedge-shaped substrate is sandwiched between adjacent dichroic filters. If the filters are in contact with each other or cemented together, the composition of the materials that determine the spectral performance of the filter may be different from those which are not in contact. Those of ordinary skill in the art will appreciate that flat, non wedge-shaped substrates could be used to fabricate the spectral dispersing filter assembly 252. In this case another means such as mechanically mounting the filters could be used to maintain the angular relationships between the filters.

Figure 19:
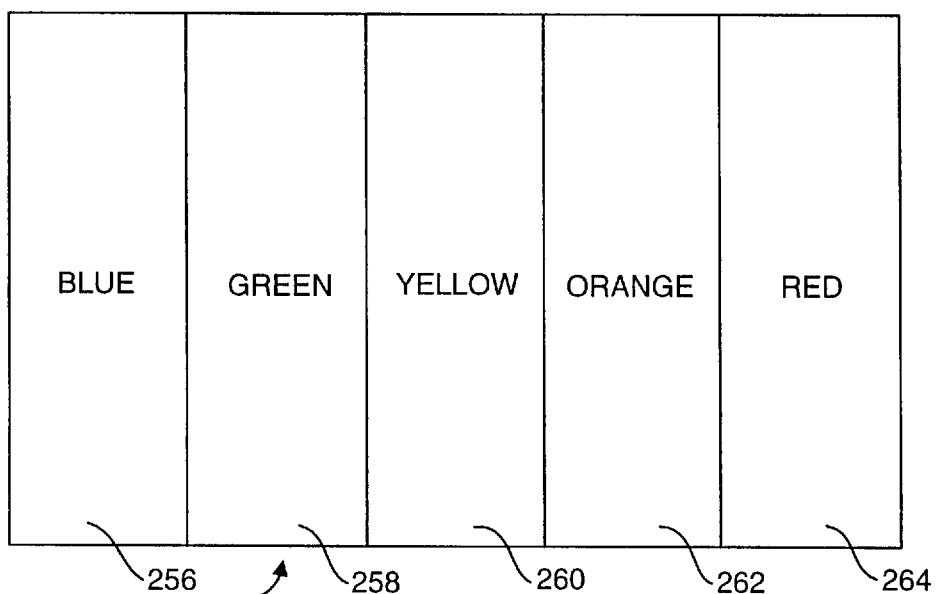
FIG. 19 is a schematic illustration of a detection filter assembly that may optionally be placed in front of the TDI detector in the embodiment of FIG. 17 to further suppress out-of-band light.
Figure 20A:
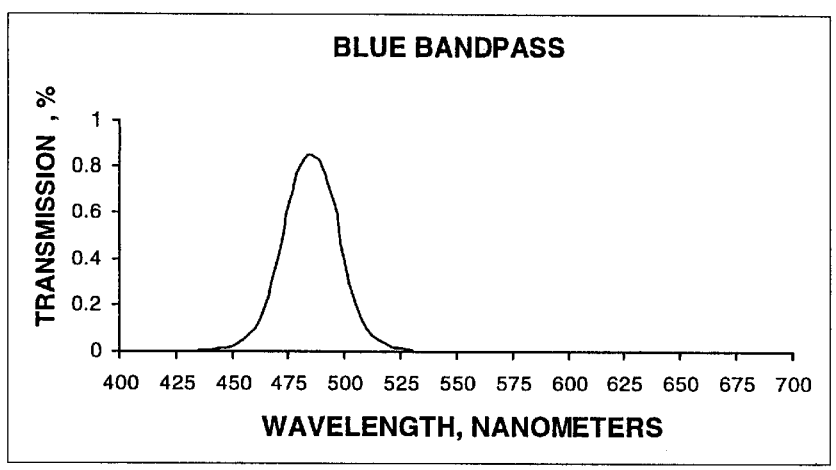
FIGS. 20A–20E are X-Y plots of transmission vs. wavelength corresponding to corresponding passbands of the filter segments of the detection filter assembly that may optionally be placed in front of the TDI detector.
Figure 20B:
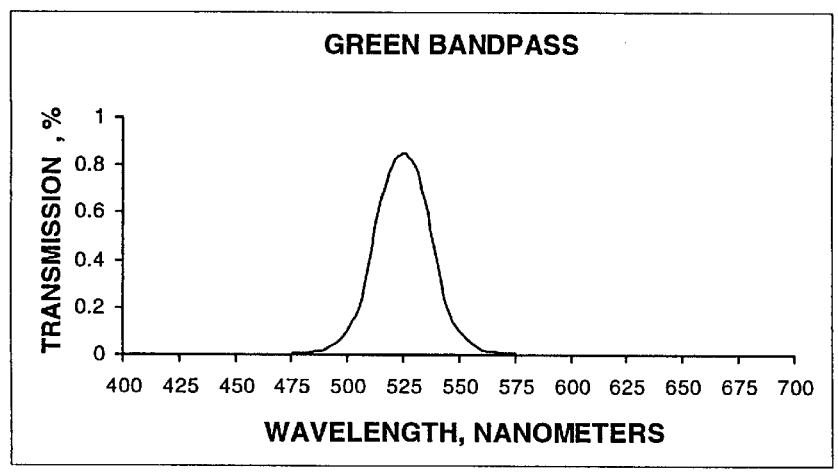
Figure 20C:
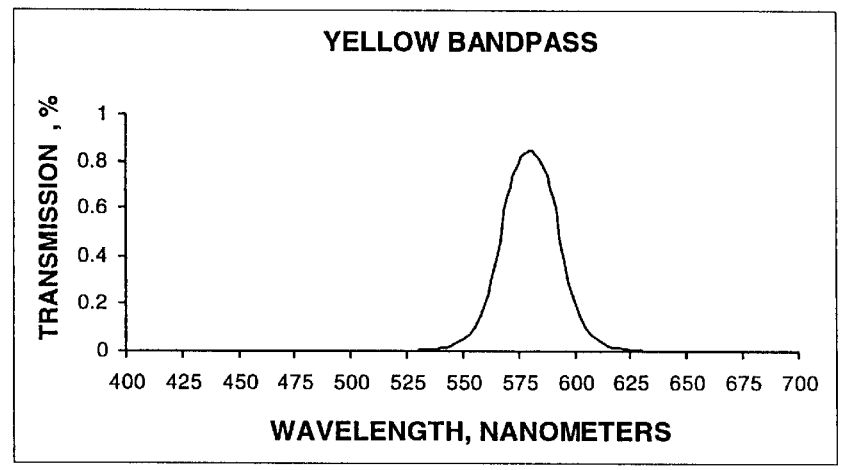
Figure 20D:
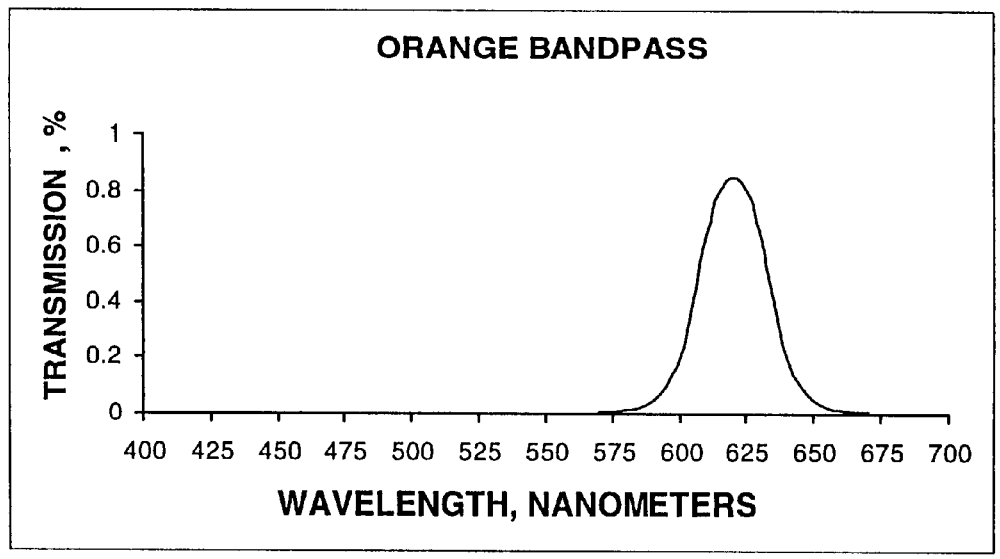
Figure 20E:
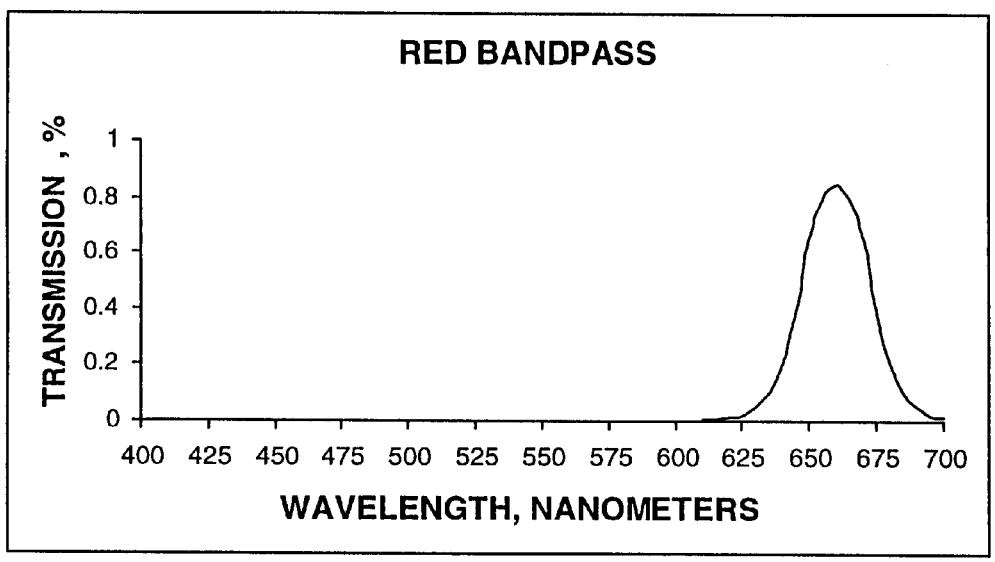

In addition to the foregoing configuration, non-distorting spectral dispersion system 250 may optionally include a detector filter assembly 254 to further attenuate undesired signals in each of the light beams, depending upon the amount of rejection required for out-of-band signals. FIG. 19 illustrates the construction of an exemplary detector filter 254 corresponding to the five color bands discussed above and includes a blue spectral region 256, a green spectral region 258, a yellow spectral region 260, an orange spectral region 262, and a red spectral region 264, all of which are disposed side-by-side, as shown in the Figure. The corresponding spectral characteristics of the blue, green, yellow, orange, and red spectral regions or wavebands are respectively shown in FIGS. 20A–20E. The detection filter assembly shown in FIG. 19 may be constructed by cementing separate filters in side-by-side arrangement on a common substrate or by other means well known to those or ordinary skill in the art. Additionally, the ordinary practitioner in the art will understand that the filter may alternatively be placed at an intermediate image plane, instead of directly in front of TDI detector 44.

Figure 21:
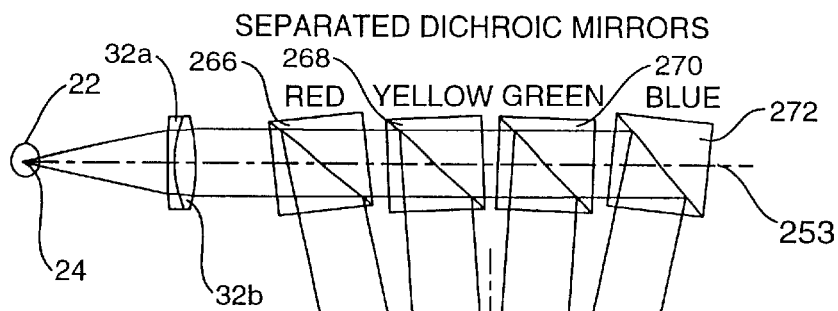
FIG. 21 is a plan view of another embodiment of the configuration of FIG. 17, wherein the spectral dispersion filter system comprises a plurality of dichroic cube filters orientated at various angles to create the spectral dispersing effect.
Figure 21:
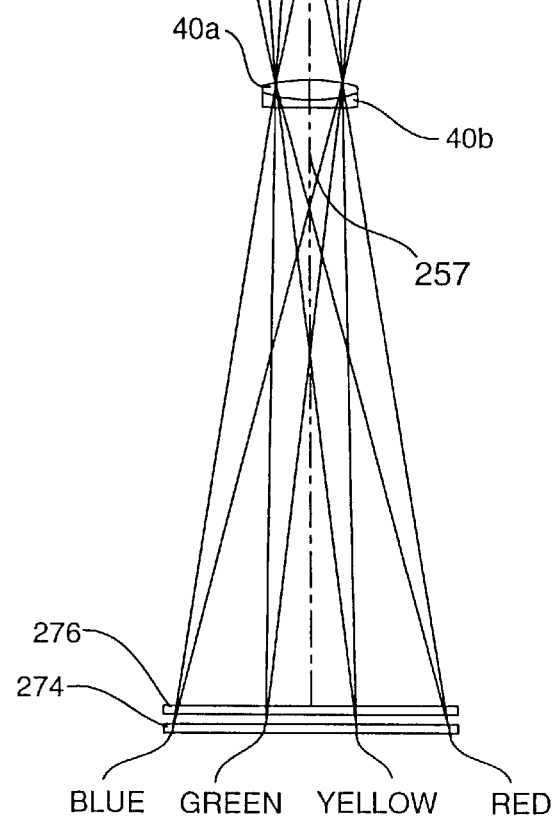

In the embodiment shown in FIG. 17, light may pass through each dichroic filter in the spectral dispersing filter assembly 252 twice before exiting spectral dispersing filter assembly 252. This condition will further attenuate out-of-band signals, but will also attenuate in-band signals. FIG. 21 illustrates an eighth embodiment of the present invention in which the light does not pass through another dichroic filter after reflection. In this embodiment, a plurality of cube dichroic filters, including a red cube filter 266, a yellow cube filter 268, a green cube filter 270, and a blue cube filter 272 are spaced apart sufficiently to ensure that light does not pass through any of the cube filters more than once. As with the embodiment of FIG. 17, the cube dichroic filters are oriented at appropriate angles to image light within a predefined bandwidth to distinct regions on a TDI detector 274. As the light is reflected from each of cube dichroic filters 266, 268, 270 and 272, it is directed toward imaging lenses 40a and 40b, and different bandpass portions of the light are focussed upon corresponding red, yellow, green, and blue light receiving segments or regions defined on a light receiving surface of TDI detector 274. If desired, an optional detector filter assembly 276 of similar construction to detector filter assembly 254 (but without the orange spectral region) may be used to increase the rejection of out-of-band signals. It should be apparent to those skilled in the art that separate spaced apart plate, or pellical beam splitters could also be used in this application instead of the cube filters. In the eight embodiment illustrated in FIG. 21, the image lenses 40a and 40b must be placed a sufficient distance away from the plurality of cube filters to minimize the clear aperture requirement for lenses 40a and 40b. Those skilled in the art will appreciate the clear aperture in the plane orthogonal to the page can increase as the distance between the lenses and plurality cube filters increases. Therefore, the placement of lenses 40a and 40b must be chosen to appropriately accommodate the clear aperture in both planes.

The foregoing descriptions of the seventh and eighth preferred embodiments illustrate the use of four and five color systems. Those skilled in the art will appreciate that a spectral dispersing component with more or fewer filters may be used in these configurations in order to construct a system covering a wider or a narrower spectral region, or different passbands within a given spectral region. Likewise, those skilled in the art will appreciate that the spectral resolution of the present invention may be increased or decreased by appropriately choosing the number and spectral characteristics of the dichroic and or bandpass filters that are used. Furthermore, those skilled in the art will appreciate that the angles or orientation of the filters may be adjusted to direct light of a given bandwidth onto any desired point on the TDI detector. In addition, there is no need to focus the light in increasing or decreasing order by wavelength. For example, in fluorescence imaging applications, one may wish to create more spatial separation on the TDI detector between the excitation and emission wavelengths by changing the angles at which the filters corresponding to those wavelengths are oriented with respect to the optic axes of the system. Finally, it will be clear to those skilled in the art that dispersion of the collected light may be performed on the basis of non-spectral characteristics, including angle, position, polarization, phase, or other optical properties.

As with the earlier embodiments discussed above, many applications of the seventh and eighth preferred embodiments will require that one or more light sources be used to provide light that is incident on the object being imaged. Accordingly, various light sources disposed at different positions, such as those shown in FIGS. 5–7 and discussed above, may be used to enhance the image quality produced by each of these embodiments. For clarity and to simplify the explanation of these embodiments, the light sources have been omitted in FIGS. 17 and 21; however, it will be recognized by those skilled in the art how such light sources may be employed in these embodiments, based on the previous discussion of the use of the light sources with respect to the earlier embodiments.

Figure 22:
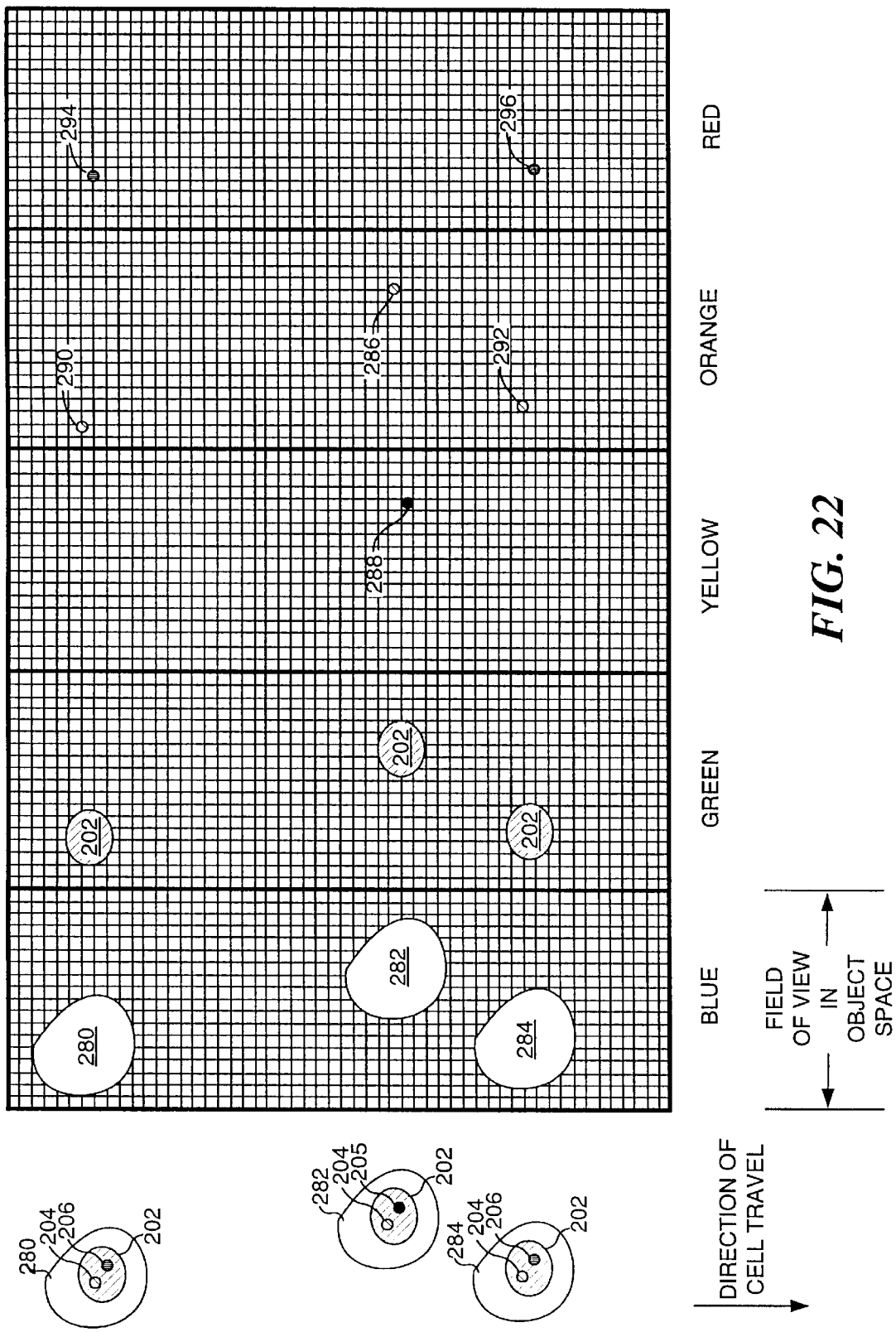
FIG. 22 illustrates an exemplary set of images projected onto the TDI detector when using the spectral dispersing filter system of the FIG. 17.

FIG. 22 illustrates the distribution of images on TDI detector 44 corresponding to imaging a plurality of cells 200 when using non-distorting spectral dispersion system 250. As will be evident by comparing FIG. 22 to FIG. 16, the resultant images on the TDI detector are similar in many ways. However, when using the non-distorting spectral dispersion system, there is no image broadening as is seen in FIG. 22, which would otherwise result due to the convolution of the emission spectrum and the object. Instead, all wavelengths within the predefined bandwidth of each dichroic filter are reflected from the filter at the same nominal angle, so image components that fall within that passband suffer no positional distortion on the detector. The field angle orthogonal to flow in object space is also indicated on FIG. 22. In this particular configuration, the field angle in object space is less than +/−0.25°. Those skilled in the art will appreciate that the field angle can be made larger or smaller. To the extent that the field angle is made larger, for example, to image cells over a wider region on a slide or in a broad flat flow, the field angle at the detector will increase in proportion to the number of colors used. FIG. 22 illustrates the image projected onto the detector when three cells 280, 282 and 284 are flowing through the field of view. Light scatter images of cells 280, 282, and 284 are seen on the left hand side of the detector denoted as the BLUE area. Images of cell nuclei 202 stained with a green fluorescent dye are seen in the GREEN area of the detector. Three differently-colored genetic probes 204, 205, and 206 are also employed for the analysis of the sex chromosomes within the cells. Probe 204 stains the X chromosome with an orange fluorescing dye, probe 205 stains the Y chromosome with yellow fluorescing dye, and probe 206 stains the inactive X chromosome in female cells with a red fluorescing dye. Cell 282 is imaged onto the detector as shown in FIG. 22. An image 286 of probe 204 from cell 282 is seen in the ORANGE area of the detector. Likewise an image 288 of probe 205 is seen in the YELLOW area of the detector. The signal on the detector is processed to determine the existence and position of these images on the detector to determine that cell 282 is a male cell. In a similar manner, cells 280 and 284 contain probes 204 and 206, which create images 290 and 292 in the ORANGE area of the detector, and images 294 and 296 in the RED area of the detector, indicating that these cells are female, respectively.

Wide-Field Decomposition Imaging

Figure 24:
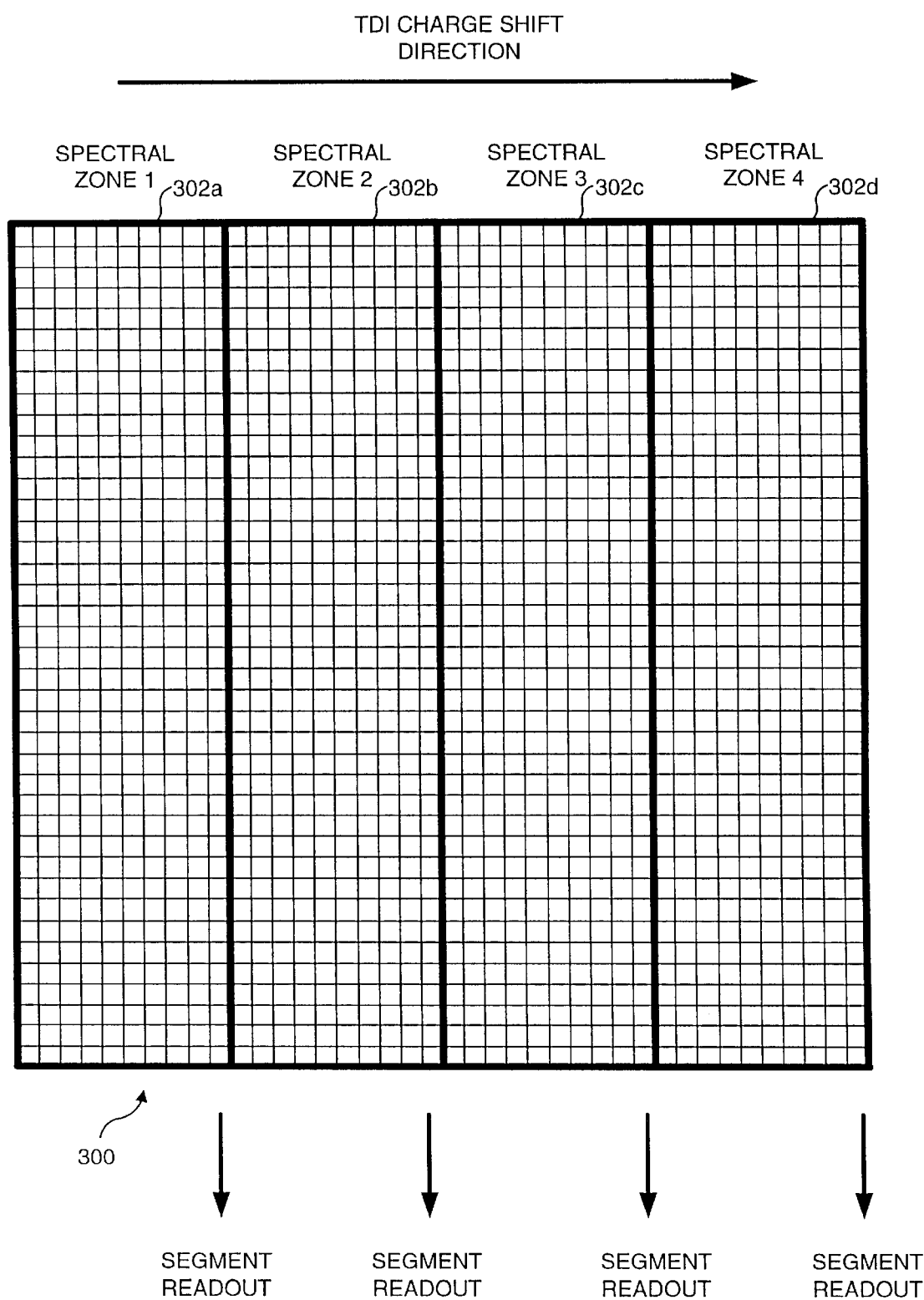
FIG. 24 is a schematic plan view of a spectrally segmented detector for use in detecting and imaging light of several different spectral compositions.

By using a segmented TDI detector 300, as shown in FIG. 24, the present invention can be used to image wide fields of view to increase throughput. In this manner, cells or other objects may be oriented side-by-side such as may be found in broad flat flow, or on microscope slides and microtiter plates. This configuration enables more objects to be imaged simultaneously than could otherwise be possible if objects were aligned in a single file orientation.

Figure 23:
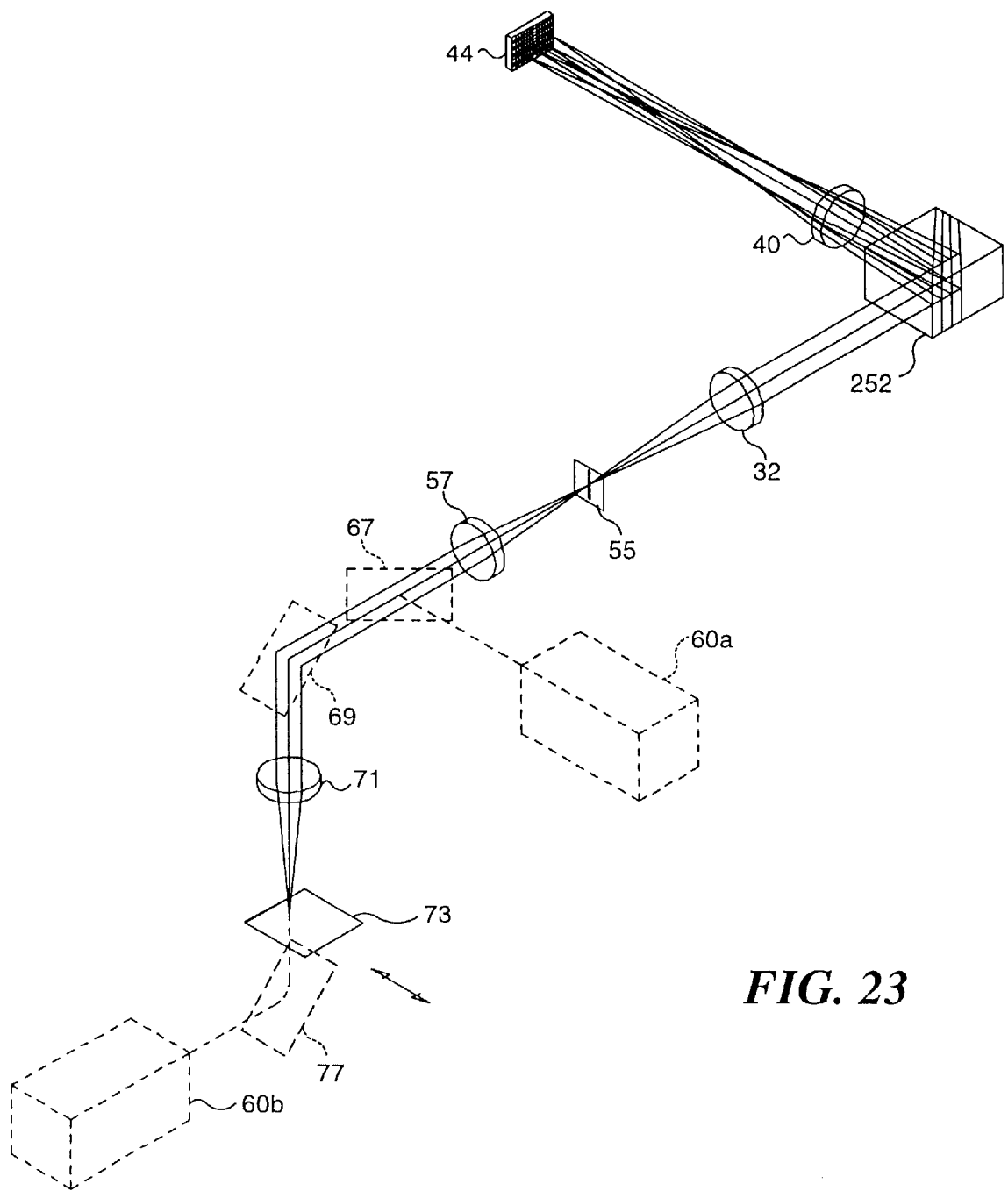
FIG. 23 is a schematic isometric view of yet another embodiment, in which spectral decomposition occurs in an axis that is generally parallel to a direction of motion of a substrate carrying an object.

FIG. 23 illustrates an embodiment of the present invention that facilitates imaging of a wide field. In FIG. 23, motion of a substrate 73 is generally parallel or aligned with an axis of spectral decomposition provided by dichroic beam splitter 252. Optional epi illuminator 60a, which may comprise a laser or other type of illumination source, can be used to illuminate objects carried on substrate 73, while there is relative movement between the substrate and the imaging system in the direction of the double-headed arrow. Optionally, another illuminator 60b is provided to provide bright field illumination of the objects on the substrate with light reflected from a reflective surface 77. Light from the objects on substrate 73 passes through a lens 71, is reflected from a reflective surface 69, passes through a dichroic (or partially reflective) mirror 67 and is focussed on a slit 55 by a lens 57. Collection lens 32 collimates the light from the slit and directs the light onto dichroic beam splitter 252, which spectrally disperses the light passing through lens 40 and onto different regions of detector 44.

Segmented detector 300 (FIG. 24) is used for detector 44 in FIG. 23, and spectral dispersing filter assembly 252 is oriented to decompose light in an axis parallel to the movement of the image across detector 44. As noted above, the field of view of substrate 73 in FIG. 23 may be illuminated in bright field with bright field illuminator 60b or with epi-illumination by illuminator 60a. In either case the illuminated field of view, when imaged by the optical system, is equivalent in size to one segment of detector 300.

As discussed previously, when spectral dispersing filter assembly 252 is employed, light is split into a plurality of light beams each having a different bandwidth. Each light beam thus produced is directed at a different nominal angle so as to fall upon a different segment of detector 300. The nominal angular separation between each bandwidth produced by spectral dispersing filter assembly 252 exceeds the field angle of the imaging system in object space, thereby preventing overlap of the field images of various bandwidths on the detector. Therefore, each detector segment sees the same field of view, however, each segment sees light composed of a different spectral bandwidth. Slit 55 may be provided to eliminate any stray light from outside the intended field of view from passing through the system and landing on an inappropriate zone of detector 300.

In the illustrated embodiment, segmented detector 300 comprises four segments or zones 302a–302d, each zone receiving light of a different characteristic. The detector is segmented into these zones such that the charge corresponding to an incident image flows across a segment in concert with the image movement across that segment The charge is then read out of the segment and not permitted to enter an adjacent segment or zone where light of a different characteristic is imaged. Optionally, the charge corresponding to an image received by each zone is integrated over a length of the zone and readout from the tap provided for the zone. Also, optionally, the rate at which the charge is readout from each zone is independently controllable. In summary, this last embodiment of the present invention enables a wide field of view to be imaged and decomposed onto the detector such that light of multiple characteristics can be simultaneously collected and analyzed.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An imaging system adapted to determine one or more characteristics of an object from an image of the object, comprising:
   (a) a collection lens disposed so that light traveling from the object passes through the collection lens and travels along a collection path;
   (b) a plurality of light reflecting elements disposed in the collection path, each light reflecting element reflecting light of a predefined characteristic and passing light that does not have that characteristic, each light reflecting element being positioned at a different angle with respect to the collection path to reflect light of the predefined characteristic in a direction different from that of other light reflecting elements, each light reflecting element being positioned adjacent to a preceding light reflecting element such that light reflected by all but a first light reflecting element passes through at least one preceding light reflecting element a second time; and
   (c) a detector disposed to receive light that has been reflected by the light reflecting elements, producing an output signal that is indicative of at least one characteristic of the object, said detector integrating the output signal over time.

2. The imaging system of claim 1, wherein wedge-shaped substrates define an angular difference between each light reflecting element, and wherein light reflecting surfaces of the light reflecting elements are sandwiched between the wedge-shaped substrates, forming a monolithic structure.

3. The imaging system of claim 1, where the light reflecting elements reflect light based on a spectral content of that light.

4. The imaging system of claim 1, where the light reflecting elements reflect light as a function of a polarization characteristic of the light.

5. The Imaging system of claim 1, wherein the collection lens substantially collimates the light that is traveling along the optical path toward a plurality of light reflective elements.

6. The imaging system of claim 1, further comprising an imaging lens disposed to receive light reflected from the plurality of reflective elements, said imaging lens producing an image of the light on the detector.

7. The imaging system of claim 1, wherein the light traveling in each different direction from each of the plurality of reflecting elements is incident on a different region of the detector.

8. The imaging system of claim 1, wherein the detector comprises a time delay and integration (TDI) detector.

9. The imaging system of claim 1, further comprising a filter disposed between the plurality of light reflective elements and the detector, said filter attenuating light that does not have the predefined characteristic of the light reflected from at least one of the plurality of light reflecting elements.

10. The imaging system of claim 9, wherein the filter comprises a plurality of spectral regions, each having a different one of the predefined characteristics of the plurality of light reflecting elements so that the light reflected from each of the plurality of light reflecting elements associated with each predefined characteristic is incident on a corresponding spectral region of the filter, said spectral region passing the light having the predefined characteristic and blocking light that does not have the predefined characteristic of said spectral region.

11. The imaging system of claim 1, wherein said detector comprises a pixelated detector.

12. A method for determining one or more characteristics of an object based upon light from the object, comprising the steps of:
   (a) focussing the light from the object along a collection path;
   (b) at each of a plurality of successive points disposed along the collection path, reflecting light of a predefined characteristic, and passing light that does not have the predefined characteristic, a different predefined characteristic being associated with each of the plurality of points so that light of a different one of the different predefined characteristics is reflected from each successive point in a direction different from that at other points, and so that light reflected at all but a first point of the plurality of successive points passes through at least one preceding point of the successive points a second time;
   (c) receiving the light that was reflected at a detector, said detector integrating an output signal over time in response thereto; and
   (d) analyzing the output signal from the detector to determine at least one characteristic of the object.

13. The method of claim 12, wherein each of the plurality of light reflecting elements associated with a specific different one of the different characteristics is disposed at each successive point, further comprising the step of joining the plurality of light reflecting elements together with intermediate wedge-shaped substrates, forming a monolithic structure that disperses the light in the different directions as a function of the different predefined characteristics associated with the plurality of light reflecting elements.

14. The method of claim 12, wherein the step of reflecting light in different directions comprises the step of reflecting the light in a specific direction based on a spectral content of the light that is thus reflected.

15. The method of claim 12, wherein the light traveling along the collection path has a plurality of different polarization characteristics, said step of reflecting comprising the step of reflecting the light in a specific direction based upon a polarization characteristic of the light that is thus reflected.

16. The method of claim 12, further comprising the step of imaging the light traveling in each different direction using a lens.

17. The method of claim 12, further comprising the step of producing a plurality of signals, each signal corresponding to an intensity of the light traveling in one of the different directions and with one of the plurality of different predefined characteristics.

18. The method of claim 12, wherein the step of detecting includes the step of providing a time delay and integration (TDI) detector for detecting the light that is reflected.

19. The method of claim 12, wherein the step of detecting further includes the step of detecting the intensity of the light traveling in each different direction on each of a plurality of spaced-apart regions on the detector.

20. The method of claim 12, further comprising the step of attenuating light reflected from each successive point that does not have the predefined characteristic associated with the successive point in the optical path from which the light was reflected.

21. The method of claim 20, wherein the step of attenuating comprises the step of filtering so that only light having the predefined characteristic associated with the successive point from which the light was reflected is allowed to pass to the detector.

22. The method of claim 12, wherein the step of focussing comprises the step of collimating the light traveling along the optical path prior to said light reaching the plurality of successive points.

23. An imaging system adapted to determine one or more characteristics of an object from an image of the object while there is relative movement between the object and the imaging system, comprising:
   (a) a collection lens disposed so that light traveling from the object passes through the collection lens and travels along a collection path;
   (b) a dispersing component comprising a plurality of light reflecting elements disposed in the collection path, each light reflecting element reflecting light of a predefined characteristic and passing light that does not have that characteristic, each light reflecting element being positioned at a different angle with respect to the collection path to reflect light of the predefined characteristic in a direction different from that of other light reflecting elements, each light reflecting element being positioned adjacent to a preceding light reflecting element such that light reflected by all but a first light reflecting element passes through at least one preceding light reflecting element a second time;
   (c) an imaging lens disposed to receive the light from the dispersing component, producing a plurality of images, each image corresponding to a different one of the directions in which light is reflected by the plurality of light reflecting elements, each image being projected by the imaging lens toward a different predetermined location; and
   (d) a detector disposed to receive the plurality of images produced by the imaging lens as the images move over a surface of the detector due to the relative movement between the object and the imaging system, producing an output that is indicative of at least one characteristic of the object, while the relative movement between the object and the imaging system occurs.

24. The imaging system of claim 23, wherein the plurality of light reflecting elements comprises a plurality of beam splitters arranged to reflect light of predetermined spectral characteristics at different predefined angles, all light from each beam splitter corresponding to a separate light beam, each light beam leaving the spectral dispersing component at a different nominal angle.

25. The imaging system of claim 24, wherein wedge-shaped substrates define an angular difference between each of the plurality of beam splitters, and wherein the plurality of beam splitters are sandwiched between the wedge-shaped substrates, forming a monolithic structure.

26. The imaging system of claim 23, wherein the dispersing component disperses light in a direction substantially orthogonal to a direction of the relative movement between the object and the imaging system.

27. The imaging system of claim 23, wherein the dispersing component disperses light in a direction substantially aligned with a direction of the relative movement between the object and the imaging system.

28. The imaging system of claim 23, wherein the detector comprises a time delay and integration (TDI) detector that is divided into a plurality of segments, each segment receiving light from a different one of the plurality of light reflecting elements.

29. The imaging system of claim 23, wherein the detector includes a plurality of taps, a signal indicative of different ones of the plurality of images received by the detector being output from corresponding different ones of the plurality of taps.

30. The imaging system of claim 29, wherein the detector has a length and a width, said width being divided into a plurality of regions, each region having a corresponding one of the plurality of taps, a charge generated in each region in response to the region receiving one of the plurality of images being integrated over the length of the detector.

31. The imaging system of claim 30, wherein a readout rate from each tap is independently controllable.

32. The imaging system of claim 23, wherein the light from the object comprises at least one of an unstimulated emission from the object, light reflected by the object, scattered light from the object, and a stimulated emission from the object.

33. The imaging system of claim 23, further comprising a light source that is disposed to provide an incident light that illuminates the object.

34. The imaging system of claim 33, wherein the light source illuminates the object with a bright field.

35. The imaging system of claim 33, further comprising a substrate on which the object is disposed.

36. An imaging system adapted to determine one or more characteristics of an object from an image of the object, comprising:
   (a) a collection lens disposed so that light traveling from the object passes through the collection lens and travels along a collection path;
   (b) a plurality of light reflecting elements disposed in the collection path, each light reflecting element reflecting light of a predefined characteristic and passing light that does not have that characteristic, each light reflecting element being positioned at a different angle with respect to the collection path to reflect light of the predefined characteristic in a direction different from that of other light reflecting elements, each light reflecting element being positioned adjacent to a preceding light reflecting element such that light reflected by all but a first light reflecting element passes through at least one preceding light reflecting element a second time; and
   (c) a time delay and integration (TDI) detector disposed to receive light that has been reflected by the light reflecting elements, producing an output signal that is indicative of at least one characteristic of the object, said detector integrating the output signal over time in response to the light from the light reflecting elements.

37. A method for determining one or more characteristics of an object based upon light from the object, comprising the steps of:
   (a) focussing the light from the object along a collection path;
   (b) at each of a plurality of successive points disposed along the collection path, reflecting light of a predefined characteristic, and passing light that does not have the predefined characteristic, a different predefined characteristic being associated with each of the plurality of points so that light of a different one of the different predefined characteristics is reflected from each successive point in a direction different from that at other points, and so that light reflected at all but a first point of the plurality of successive points passes through at least one preceding point of the successive points a second time;
   (c) receiving the light that was reflected at a detector, said detector including a plurality of taps and having a length and a width, said width being divided into a plurality of regions, each region having a corresponding one of the plurality of taps, a charge generated in each region in response to the region receiving light from one of the points being integrated over the length of the detector to produce an output signal; and (d) analyzing the output signal from at least one of the plurality of taps of the detector to determine at least one characteristic of the object.

38. An imaging system adapted to determine one or more characteristics of an object from an image of the object while there is relative movement between the object and the imaging system, comprising:

(a) a collection lens disposed so that light traveling from the object passes through the collection lens and travels along a collection path;

(b) a dispersing component comprising a plurality of light reflecting elements disposed in the collection path, each light reflecting element reflecting light of a predefined characteristic and passing light that does not have that characteristic, each light reflecting element being positioned at a different angle with respect to the collection path to reflect light of the predefined characteristic in a direction different from that of other light reflecting elements, each light reflecting element being positioned adjacent to a preceding light reflecting element such that light reflected by all but a first light reflecting element passes through at least one preceding light reflecting element a second time;

(c) an imaging lens disposed to receive the light from the dispersing component, producing a plurality of images, each image corresponding to a different one of the directions in which light is reflected by the plurality of light reflecting elements, each image being projected by the imaging lens toward a different predetermined location; and (d) a detector disposed to receive the plurality of images produced by the imaging lens, said detector including a plurality of taps and having a length and a width, said width being divided into a plurality of regions, each region having a corresponding one of the plurality of taps, a charge generated in each region in response to the region receiving light for one of the images being integrated over the length of the detector to produce an output signal at one of the plurality of taps that is indicative of at least one characteristic of the object.

39. An imaging system adapted to determine one or more characteristics of an object in a broad, flat flow, from an image of the object, comprising:

(a) a collection lens having a field angle in an object space that is sufficiently large to collect light traveling from the object that is in the broad, flat flow so that the light passes through the collection lens and travels along a collection path;

(b) a plurality of light reflecting elements disposed in the collection path, each light reflecting element reflecting light of a predefined characteristic and passing light that does not have that characteristic, each light reflecting element being positioned at a different angle with respect to the collection path to reflect light of the predefined characteristic in a direction different from that of other light reflecting elements, each light reflecting element being positioned adjacent to a preceding light reflecting element such that light reflected by all but a first light reflecting element passes through at least one preceding light reflecting element a second time; and (c) a detector disposed to receive light that has been reflected by the light reflecting elements, producing an output signal that is indicative of at least one characteristic of the object, said detector integrating the output signal over time.

40. An imaging system adapted to determine one or more characteristics of an object in a broad, flat flow, from an image of the object while there is relative movement between the object and the imaging system comprising:

(a) a collection lens having a field angle in an object space that is sufficiently large to collect light traveling from the object that is in the broad, flat flow so that the light passes through the collection lens and travels along a collection path;

(b) a plurality of light reflecting elements disposed in the collection path, each light reflecting element reflecting light of a predefined characteristic and passing light that does not have that characteristic, each light reflecting element being positioned at a different angle with respect to the collection path to reflect light of the predefined characteristic in a direction different from that of other light reflecting elements, each light reflecting element being positioned adjacent to a preceding light reflecting element such that light reflected by all but a first light reflecting element passes through at least one preceding light reflecting element a second time;

(c) an imaging lens disposed to receive the light beams from the dispersing component, producing a plurality of images corresponding to each of the light beams, each image being projected by the imaging lens toward a different predetermined location; and (d) a time delay integration (TDI) detector disposed to receive the plurality of images produced by the imaging lens, producing an output signal that is indicative of at least one characteristic of the object in the broad, flat flow, said TDI detector producing the output signal by integrating light from at least a portion of the object over time, while the relative movement between the object and the imaging system occurs.

* * * * *

UNITED STATES PATENT AND TRADEMARK OFFICE
CERTIFICATE OF CORRECTION

PATENT NO.    : 6,473,176 B2
DATED         : October 29, 2002
INVENTOR(S)   : Basiji et al.

It is certified that error appears in the above-identified patent and that said Letters Patent is hereby corrected as shown below:

<u>Column 26,</u>
Line 17, "claim 33" should read -- claim 23 --

Signed and Sealed this

Twenty-second Day of April, 2003

JAMES E. ROGAN
*Director of the United States Patent and Trademark Office*